United States Patent [19]

Takaya et al.

[11] Patent Number: 4,582,908
[45] Date of Patent: Apr. 15, 1986

[54] 1-SUBSTITUTED-5-THIOL-TETRAZOLE INTERMEDIATES

[75] Inventors: Takao Takaya, Kawanishi; Yoshikazu Inoue, Amagasaki; Nobuyoshi Yasuda; Masayoshi Murata, both of Mino, all of Japan

[73] Assignee: Fujisawa Pharmaceutical Co., Ltd., Osaka, Japan

[21] Appl. No.: 652,018

[22] Filed: Sep. 19, 1984

Related U.S. Application Data

[62] Division of Ser. No. 517,448, Jul. 26, 1983, Pat. No. 4,493,834, which is a division of Ser. No. 209,998, Nov. 24, 1980, Pat. No. 4,420,477.

[30] Foreign Application Priority Data

Nov. 30, 1979 [GB] United Kingdom ............... 7941417

[51] Int. Cl.$^4$ .............................. C07D 257/04
[52] U.S. Cl. ...................... 548/251; 544/26; 544/27
[58] Field of Search ........................ 548/251

[56] References Cited

U.S. PATENT DOCUMENTS 4,286,089 8/1981 Berges ...................... 548/251
4,420,477 12/1983 Takaya ...................... 544/27
4,493,834 1/1985 Takaya ...................... 544/27

FOREIGN PATENT DOCUMENTS 95029 11/1983 European Pat. Off. ........... 548/251
70763 6/1976 Japan .................... 548/251

Primary Examiner—Donald G. Daus
Assistant Examiner—Robert Benson
Attorney, Agent, or Firm—Oblon, Fisher, Spivak, McClelland & Maier

[57] ABSTRACT

This invention relates to the intermediates of formula

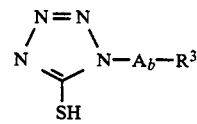

wherein $A_b$ is hydroxy (lower) alkylene, amino (lower) alkylene, protected amino (lower) alkylene, lower alkenylene, lower alkylene having an oxo group, or hydroxyimino (lower) alkylene wherein the hydrogen atom of the hydroxyimino group may be replaced with a lower aliphatic hydrocarbon group, and $R^3$ is carboxy or a protected carboxy group, and a salt thereof.

2 Claims, No Drawings

1-SUBSTITUTED-5-THIOL-TETRAZOLE INTERMEDIATES

This is a division of application Ser. No. 517,448 filed July 26, 1983, now U.S. Pat. No. 4,493,834 which is a division of Ser. No. 209,988 filed Nov. 24, 1980 now is U.S. Pat. No. 4,420,477.

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

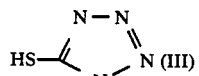

(I)

wherein
$R^1$ is amino or a substituted amino group;
$R^2$ is carboxy or a protected carboxy group;
A is hydroxy(lower)alkylene, amino(lower)alkylene, protected amino(lower)alkylene, hydroxyimino(lower)alkylene wherein the hydrogen atom of the hydroxyimino group may be replaced with a lower aliphatic hydrocarbon group, or lower alkenylene; and
$R^3$ is carboxy or a protected carboxy group.

As to the object compounds (I) and the starting compounds of the present invention, it is to be understood that there may be one or more stereoisomeric pair(s) such as optical and/or geometrical isomers due to asymmetric carbon atom(s) and/or double bond(s), in the molecule, and these isomers are also included within the scope of the present invention.

The particulars of such isomers will be made more clear in the following explanation.

According to the present invention, the object compounds (I) can be prepared by the following processes which are illustrated in the following scheme.

Process 1

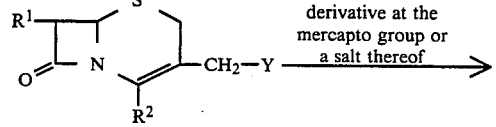

(II)
or a salt thereof

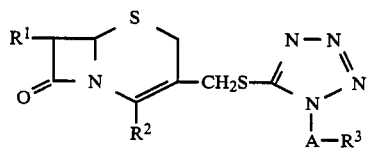

(III)
or its reactive derivative at the mercapto group or a salt thereof

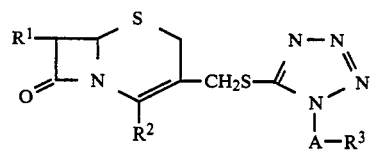

(I)
or a salt thereof

Process 2

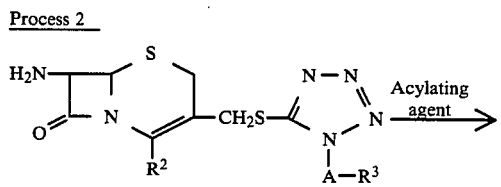

(Ib)
or its reactive derivatives at the amino group or a salt thereof

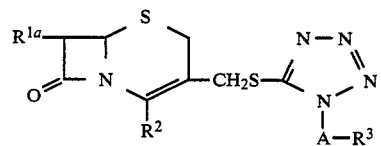

(Ia)
or a salt thereof

Process 3

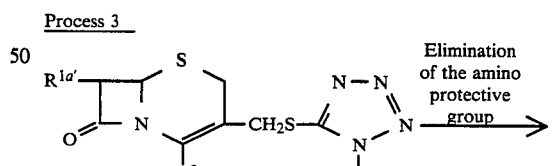

(Id)
or a salt thereof

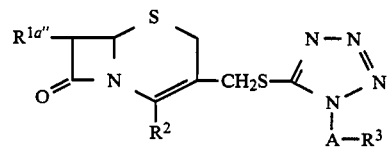

(Ic)
or a salt thereof

Process 4

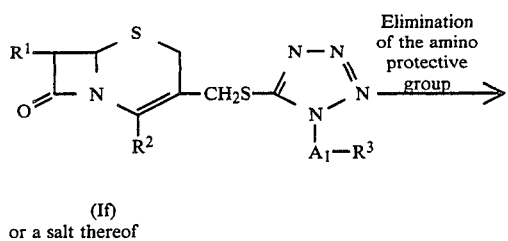

(If)
or a salt thereof

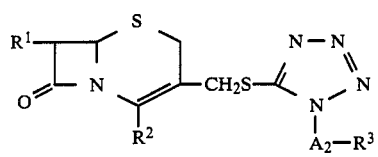

(Ie)
or a salt thereof wherein $R^1$, $R^2$, $R^3$ and A are each as defined above, Y is a group which can be substituted by a group of the formula:

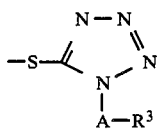

(wherein A and $R^3$ are each as defined above)

$R^{1a}$ is acylamino;

$R^{1a'}$ is acylamino having a protected amino group;

$R^{1a''}$ is acylamino having an amino group;

$A_1$ is a protected amino(lower)alkylene; and $A_2$ is amino(lower)alkylene.

Among the starting compounds in the present invention, the compound (III) and a part of the acylating agent are novel and can be prepared by the processes which are illustrated in the following scheme.

Process A

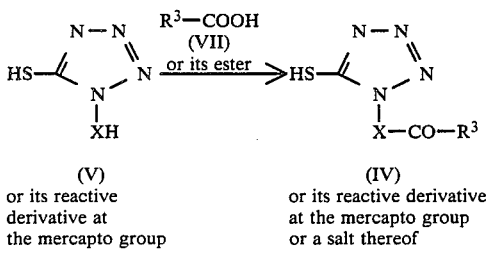

(V)
or its reactive derivative at the mercapto group (IV)
or its reactive derivative at the mercapto group or a salt thereof

Process B (i) (optional process) elimination of the carboxy protective group (IV)
or its reactive derivative at the mercapto group or a salt thereof (ii)
$H_2N-OR^4$
(VIII)
or a salt thereof

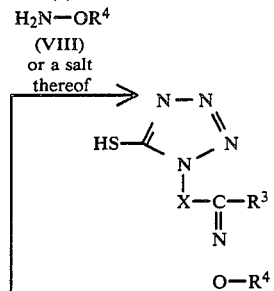

(IIIa)
or its reactive derivative at the mercapto group or a salt thereof (iii)
Reduction

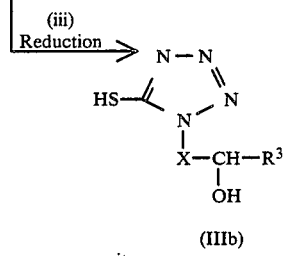

(IIIb)
or its reactive derivative at the mercapto group or a salt thereof

Process C

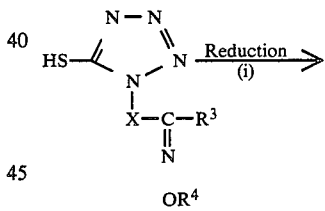

(IIIa)
or its reactive derivative at the mercapto group or a salt thereof

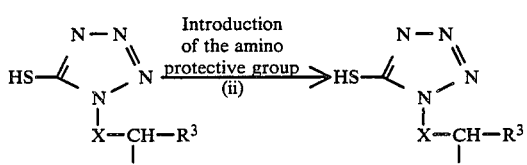

(IIId)
or its reactive derivative at the mercapto group or a salt thereof

Introduction of the amino protective group (ii)

(IIIc)
or its reactive derivative at the mercapto group or a salt thereof

Process D

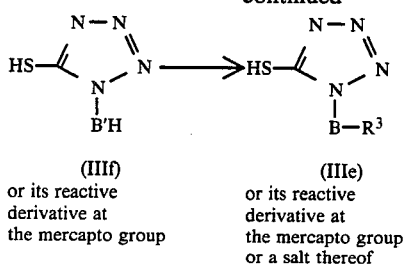

(IIIf)
or its reactive
derivative at
the mercapto group (IIIe)
or its reactive
derivative at
the mercapto group
or a salt thereof Process E

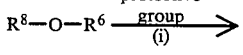

(XI)

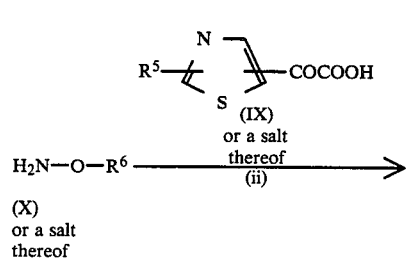

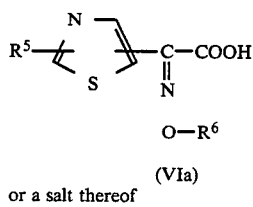

wherein
$R^3$ is as defined above;
X is lower alkylene;
$R^4$ is hydrogen or a lower aliphatic hydrocarbon group;
Z is a protected amino group;
B is lower alkenylene;
B' is lower alkenylene;
$R^5$ is amino or a protected amino group; and
$R^6$ is an organic residue which may have suitable substituent(s),
$R^8$ is amino having a protective group.

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

The term "halogen" includes fluorine, chlorine, bromine and iodine.

Suitable "substituted amino group" for $R^1$ may include an amino group substituted by a conventional substituent used in Cephalosporin and Penicillin compounds such as acyl as mentioned below, ar(lower)alkyl (e.g. benzyl, phenethyl, trityl, etc.) or the like.

Suitable "acylamino" in the terms "acylamino" as the suitable substituted amino groups for $R^1$, "acylamino" for $R^{1a}$, "acylamino having a protected amino group" for $R^{1a'}$ and "acylamino having an amino group" for $R^{1a''}$ may include the group of the formula:

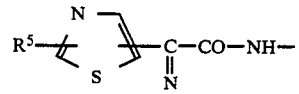

wherein $R^5$ and $R^6$ are each as defined above.

In the connection, as we stated above, it is to be understood that the object compounds (I), (Ia), (Ic), (Id), (Ie) and (If) and the starting compounds (II), (VIa) and (IX) include tautomeric isomers. That is, in case that the group of the formula:

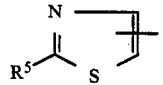

($R^5$ is as defined above) is contained in the molecules of said object and starting compounds, said group of the formula can also be alternatively represented by its tautomeric formula:

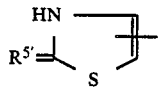

($R^{5'}$ is imino or a protected imino group). That is, the both of said groups are in the state of equilibrium each other and such tautomerism can be represented by the following equilibrium.

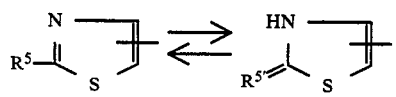

wherein $R^5$ and $R^{5'}$ are each as defined above.

These types of tautomerism between the amino-compound and the corresponding imino-compound as stated above have been well known in the literature, and it is obvious to a person skilled in the arts that both of the tautomeric isomers are easily convertible reciprocally and are included within the same category of the compound per se. Accordingly, the both of the tautomeric forms of the object compounds (I), (Ia), (Ic), (Id), (Ie) and (If) and the starting compounds (II), (VIa) and (IX) are clearly included within the scope of the present invention. In the present specification and claims, the object and starting compounds including the group of such tautomeric isomers are represented by using one of the exressions therefor, that is the formula:

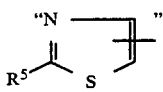

wherein R⁵ is as defined above.

Furthermore, with regard to the object compounds (I), (Ia), (Ib), (Ic), (Id), (Ie) and (If) and the starting compounds (II), (III), (IIIa) and (VIa), it is also to be noted that where the oxyimino group(s) is contained in the chemical structure thereof, and these compounds exist as geometrical isomers, i.e. syn isomer, anti isomer and a mixture thereof. For example, with regard to the object compound (I), the syn isomer in the 7-position means one geometrical isomer having the partial structure represented by the following formula:

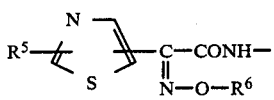

(wherein R⁵ and R⁶ are each as defined above) and the anti isomer in the 7-position means the other geometrical isomer having the partial structure represented by the following formula:

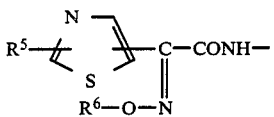

(wherein R⁵ and R⁶ are each as defined above).

On the other hand, the syn isomer in the 3-position means one geometrical isomer having the partial structure represented by the following formula:

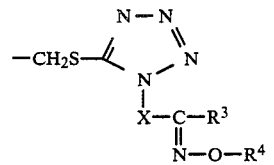

(wherein R³, R⁴ and X are each as defined above) and the anti isomer in the 3-position means one geometrical isomer having the partial structure represented by the following formula:

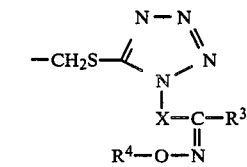

(wherein R³, R⁴ and X are each as defined above).

Regarding the other object and starting compounds as mentioned above, the syn isomer and the anti isomer can also be referred to the same geometrical isomers as illustrated for the compound (I).

In this regard, the above formula:

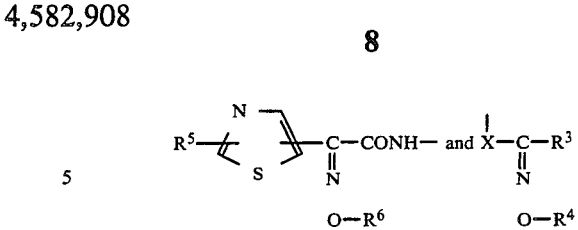

(wherein R³, R⁴, R⁵, R⁶ and X are each as defined above) are intended to represent both of the syn isomer and anti isomer as well as a mixture thereof and both of the respective isomers as well as a mixture thereof are included within the scope of the present invention.

Suitable "protected amino" in the terms "protected amino" for $R^5$ and Z, "acylamino having a protected amino group" for $R^{1a'}$ and "protected amino lower alkylene" for A and $A_1$ may include an acylamino or an amino group substituted by a conventional protecting group such as ar(lower)alkyl which may have at least one suitable substituent(s), (e.g. benzyl, trityl, etc.) or the like.

Suitable "acyl" and "acyl moiety" in the term "acylamino" may include carbamoyl, an aliphatic acyl group, an acyl group containing an aromatic ring (hereinafter referred to as aromatic acyl) and an acyl group containing a heterocyclic ring (hereinafter referred to as heterocyclic acyl).

Suitable example of said acyl may be illustrated as follows:

Aliphatic acyl such as lower or higher alkanoyl (e.g. formyl, acetyl, succinyl, hexanoyl, heptanoyl, stearoyl, etc.); lower or higher alkoxycarbonyl (e.g. methoxycarbonyl, ethoxycarbonyl, tert-butoxycarbonyl, tert-pentyloxycarbonyl, heptyloxycarbonyl, etc.); lower or higher alkanesulfonyl (e.g. methanesulfonyl, ethanesulfonyl, etc.); or the like.

Aromatic acyl such as aroyl (e.g. benzoyl, toluoyl, naphthoyl, etc.);
ar(lower)alkanoyl (e.g. phenylacetyl, phenylpropionyl, etc.);
aryloxycarbonyl (e.g. phenoxycarbonyl, naphthyloxycarbonyl, etc.);
ar(lower)alkoxycarbonyl (e.g. benzyloxycarbonyl, phenethyloxycarbonyl, etc.);
aryloxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonyl, etc.); or the like;

Heterocyclic aryl such as heterocycliccarbonyl (e.g. thenoyl, furoyl, nicotinoyl, etc.);
heterocyclic(lower)alkanoyl (e.g. thienylacetyl, thiazolylacetyl, thiadiazolylacetyl, dithiinylacetyl, pyridylacetyl, pyrimidinylacetyl, triazolylacetyl, tetrazolylacetyl, furylacetyl, oxazolylacetyl, thiazolylpropionyl, etc.);
heterocyclicglyoxyloyl (e.g. thiazolylglyoxyloyl, thienylglyoxyloyl, etc.); or the like.

The acyl and acyl moiety as stated above may have one or more, same or different, suitable substituent(s) such as lower alkyl as mentioned below;
lower alkoxy (e.g. methoxy, ethoxy, propoxy, etc.);
lower alkylthio (e.g. methylthio, ethylthio, etc.);
lower alkylamino (e.g. methylamino, etc.);
halogen (e.g. chlorine, bromine, fluorine or iodine);
amino; a protected amino group as mentioned below:;
hydroxy; a protected hydroxy such as tetrahydropyranyloxy or acyloxy wherein the acyl moiety is as stated above; imino; oxo;

a group of the formula: =N—OR$^6$ wherein R$^6$ is as defined above; or the like.

Suitable "organic residue which may have suitable substituent(s)" for R$^6$ may include an aliphatic and aromatic group, for example, lower alkyl (e.g. methyl, ethyl, propyl, isopropyl, butyl, isobutyl, tert-butyl, pentyl, neopentyl, tertpentyl, hexyl, etc.);

lower alkenyl (e.g. vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.);

lower alkynyl (e.g. ethynyl, 1-propynyl, 2-propynyl, 1-methyl-2-propynyl, 1 or 2 or 3-butynyl, 1 or 2 or 3 or 4-pentynyl, 1 or 2 or 3 or 4 or 5-hexynyl, etc.);

cycloalkyl (e.g. cyclopropyl, cyclobutyl, cyclopentyl, cyclohexyl, cycloheptyl, etc.);

cyclo(lower)alkenyl (e.g. cyclopropenyl), cyclobutenyl, cyclopentenyl, cyclohexenyl, etc.);

aryl (e.g. phenyl, tolyl, xylyl, cumenyl, naphthyl, etc.);

ar(lower)alkyl such as phenyl(lower)alkyl (e.g. benzyl, phenethyl, phenylpropyl, etc.);

ar(lower)alkyl having at least one suitable substituent(s) such as halogen as mentioned above (e.g. chlorobenzyl, dichlorobenzyl, trichlorobenzyl, fluorobenzyl, fluorophenetyl, fluorophenylpropyl, etc.) or the like.

Suitable protected carboxy for R$^2$ and R$^3$ may include an esterified carboxy and the like, and suitable examples of the ester moiety in said esterified carboxy may be the ones such as lower alkyl ester (e.g. methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono(or di or tri)-halo(lower-)alkyl ester (e.g. 2-iodoethyl ester, 2,2,2-trichloroethyl ester, etc.); lower alkenyl ester (e.g. vinyl ester, allyl ester, etc.);

lower alkynyl ester (e.g. ethynyl ester, propynyl ester, etc.);

ar(lower)alkyl ester which may have at least one suitable substituent(s) (e.g. benzyl ester, 4-methoxybenzyl ester, 4-nitrobenzyl ester, phenethyl ester, trityl ester, diphenylmethyl ester, bis-(methoxyphenyl)-methyl ester, 3,4-dimethoxybenzyl ester, 4-hydroxy-3,5-ditertiarybutylbenzyl ester, etc.);

aryl ester which may have at least one suitable substituent(s) (e.g. phenyl ester, 4-chlorophenyl ester, tolyl ester, tertiarybutylphenyl ester, xylyl ester, mesityl ester, cumenyl ester, etc.), and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.) and phenyl(lower)alkoxycarbonyl (e.g. benzyloxycarbonyl, diphenylmethoxycarbonyl, etc.).

Suitable "lower alkylene" in the terms "hydroxy(-lower)alkylene", "amino(lower)alkylene", "protected amino(lower)alkylene", "hydroxyimino(lower)alkylene" wherein the hydrogen atom of the hydroxyimino group may be replaced with a lower aliphatic hydrocarbon group for A, a protected amino(lower)alkylene for A$_1$, amino(lower)-alkylene for A$_2$, lower alkylene for X, may include straight or branched one and may include methylene, ethylene, trimethylene, propylene, tetramethylene, pentamethylene, hexamethylene and the like.

Suitable "lower aliphatic hyrocarbon group" in the terms "hydroxyimino(lower)alkylene wherein the hydrogen atom of the hydroxyimino group may be replaced with a lower aliphatic hydrocarbon group" for A and "a lower aliphatic hydrocarbon group" for R$^4$ may include a monovalent radical of a saturated or unsaturated, and straight or branched acyclic aliphatic hydrocarbon, and particularly may include lower alkyl, lower alkenyl, lower alkynyl and the like, each of which is exemplified for R$^6$.

Suitable "lower alkenylene" for A, B and B' means straight or branched one and may include lower alkenylene (e.g. vinylene, 1-propenylene, 2-propenylene, 1-methyl-2-propenylene, 1 or 2 or 3-butenylene, 1 or 2 or 3 or 4-pentenylene, 1 or 2 or 3 or 4 or 5-hexenylene, etc.) and lower alkenylidene (e.g. vinylidene, propenylidene, butenylidene, pentenylidene, hexenylidene, etc.).

In this connection, with regard to the object compounds (I), (Ia), (Ib), (Ic) and (Id) and starting compounds (III) and (IIIe), it is to be noted that when the group represented by A is lower alkenylene, there is a possibility that these compounds exist as geometrical isomers, i.e. cis- and trans-isomers and a mixture thereof. For example, with regard to the object compound (I) wherein the group represented by -A-R$^3$ is 3-carboxy-1-propenyl, the cis isomer means one geometrical isomer having the partial structure represented by the following formula:

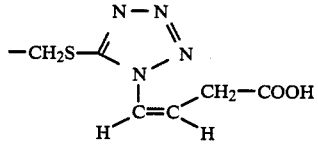

and the trans isomer means the other geometrical isomer having the partial structure represented by the following formula:

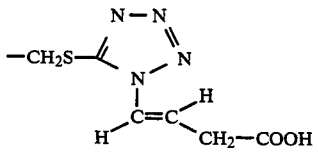

The cis-and trans-isomers as well as a mixture thereof are included within the scope of the present invention.

Suitable example of Y may include an acid residue (e.g. azido, halogen as mentioned above, acyloxy as mentioned above, etc.) and the like.

Suitable "amino having a protective group" for R$^8$ may include phthalimido, succinimido, ethoxycarbonylamino and the like, and preferably phthalimido.

The preferable examples of the object compound (I) are exemplified as follows:

Preferably example of $R^1$ is amino or acylamino, for example, a group of the formula:

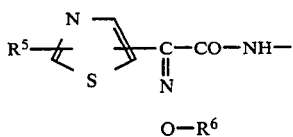

wherein
$R^5$ is amino, lower alkanoylamino or halogen substituted lower alkanoylamino;
$R^6$ is lower alkyl, lower alkenyl, lower alkynyl, cycloalkyl, cyclo(lower)alkenyl, aryl[more preferably, phenyl], ar(lower)alkyl[more preferably, phenyl(lower)alkyl] or ar(lower)alkyl having halogen [more preferably, phenyl(lower)alkyl having halogen];
$R^2$ is carboxy;
$R^3$ is carboxy; and
A is hydroxy(lower)alkylene, amino(lower)alkylene, acylamino(lower)alkylene[more preferably lower alkoxycarbonylamino(lower)alkylene], hydroxyimino(lower)alkylene, lower alkoxyimino(lower)alkylene, lower alkenyloxyimino(lower)alkylene, lower alkenylene or lower alkenylidene.

The processes for preparing the object compounds of the present invention are explained in detail in the following.

PROCESS 1

The object compound (I) or a salt thereof can be prepared by reacting the compound(II) or a salt thereof with the compound (III) or its reactive derivative at the mercapto group or a salt thereof.

Suitable salts of the compound (II) and (III) are each referred to the ones exemplified for the compound (I).

Suitable reactive derivative at the mercapto group in the compound (III) may include a metal salt such as an alkali metal salt (e.g. sodium salt, potassium salt, etc.), an alkaline earth metal salt (e.g., magnesium salt, etc.) or the like.

The reaction is usually carried out in a solvent such as water, acetone, chloroform, nitrobenzene, methylene chloride, ethylene chloride, dimethylformamide, methanol, ethanol, ether, tetrahydrofuran or any other conventional solvents which do not adversely influence the reaction, preferably in ones having strong polarity, which may be used as a mixture with water.

When the compound (II) and/or the compound (III) are used in free form in the reactions, the reaction is preferably carried out in the presence of a base such as alkali metal hydroxide, alkali metal carbonate, alkali metal bicarbonate, trialkylamine, pyridine, or a Lewis acid such as boron trifluoride or the like, and preferably carried out around neutral conditions. The reaction temperature is not critical and the reaction is usually carried out at ambient temperature or under warming.

The present invention includes, within its scope, the cases that a protected amino and/or a protected carboxy group are converted into the corresponding free amino and/or the free carboxy group during the reaction or the post-treating step of the present process.

PROCESS 2

The object compound (Ia) or a salt thereof can be prepared by reacting the compound (Ib) or its reactive derivatives at the amino group or a salt thereof with an acylating agent.

Suitable reactive derivatives at the amino group of the compound (Ib) may include conventional ones such as Schiff's base type imino or its tautomeric enamine type derivatives formed by the reaction of the compound (Ib) with a carbonyl compound (e.g. aldehyde, ketone, etc.), isocyanate;

silyl derivatives formed by the reaction of the compound (Ib) with a silyl compound [e.g. bis(trimethylsilyl)acetamide, trimethylsilylacetamide, etc.];

derivatives formed by the reaction of the compound (Ib) with phosphorus trichloride or phosgene, or the like.

Suitable salts of the compound (Ib) can be referred to the ones as exemplified for the compound (I).

The acylating agent to be used for the present reaction may include one of the formulae:

$$R^7\text{—OH} \qquad (VI)$$

wherein $R^7$ is acyl, or its reactive derivatives or a salt thereof.

Suitable acyls can be referred to those exemplified hereinbefore.

Suitable reactive derivatives of the compound (VI) may include an acid halide, an acid anhydride, an activated amide, an activated ester, and the like.

The suitable example may be an acid chloride; an acid azide;

a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.);

a symmetrical acid anhydride;

an activated amide with imidazole, 4-substituted imidazole, dimethylpyrazole, triazole or tetrazole; an activated ester [e.g. cyanomethyl ester, methoxymethyl ester, dimethyliminomethyl $[(CH_3)_2N=CH-]$ ester, vinyl ester, propargyl ester, p-nitrophenyl ester, 2,4-dinitrophenyl ester, trichlorophenyl ester, pentachlorophenyl ester, mesyl-phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)pyridone, N-hydroxysuccinimide, N-hydroxyphthalimide or 1-hydroxy-6-chloro-1H-benzotriazole, and the like.

These reactive derivatives can optionally be selected from them according to the kind of the compound (VI) to be used.

The salts of the compound (VI) may be salt with an inorganic base such as an alkali metal salts (e.g. sodium or potassium salt) or an alkaline earth metal salt (e.g. calcium or magnesium salt), a salt with an organic such as trimethylamine, triethylamine, dicyclohexylamine or the like.

The present reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. Among these solvents, hydrophilic solvents may be used in a mixture with water.

When the acylating agent is used in a free acid form or its salt form in the reaction, the reaction is preferably carried out in the presence of a conventional condensing agent such as carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonylbis(2-mesylimidazole), pentamethyleneketene-N-cyclohexylamine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethylbenzisoxazolium salt, N-ethyl-5-phenyl-isoxazolium-3'-sulfonate, 1-(p-chlorobenzenesulfonyloxy)-6-chloro-1H-benzotriazole, Vilsmeier reagent [e.g. (chloro-methylene)dimethylammonium chloride, a compound formed by the reaction of dimethylformamide with phosphorus oxychloride, etc.] or the like.

The reaction may also be carried out in the presence of an inorganic or an organic base such as an alkali metal bicarbonate, alkali metal carbonate, tri(lower)alkylamine, pyridine, di(lower)alkylpyridine, N-(lower)alkylmorphorine, N,N-di(lower)alkylbenzylamine, N,N-di(lower)alkylaniline, or the like. When the base or the condensing agent is in liquid, it can be used also as a solvent. The reaction temperature is not critical, and the reaction is usually carried out under cooling or at ambient temperature.

PROCESS 3

The object compound (Ic) or a salt thereof can be prepared by subjecting the compound (Id) or a salt thereof to the elimination reaction of the amino protective group.

Suitable salts of the compound (Id) may include a metal salt, ammonium salt, an organic amine salt and the like as aforementioned.

The present elimination reaction is carried out in accordance with a conventional method such as hydrolysis; reduction; elimination using a Lewis acid; a method by reacting the compound (Id), wherein the protective group is an acyl group, with an iminohalogenating agent and then with an iminoetherifying agent, and, if necessary, subjecting the resulting compound to hydrolysis; or the like.

The hydrolysis may include a method using an acid or base or hydrazine and the like. These methods may be selected depending on the kind of the protective groups to be eliminated.

Among these methods, hydrolysis using an acid is one of the common and preferable methods for elimination of an acyl group.

Suitable acid may include an organic or an inorganic acid, for example, formic acid, trifluoroacetic acid, benzenesulfonic acid, p-toluenesulfonic acid, hydrochloric acid and the like, and preferable acids are those which can easily be removed from the reaction mixture by a conventional manner such as distillation under reduced pressure, for example, formic acid, trifluoroacetic acid, hydrochloric acid, etc. The acid suitable for the reaction can be selected according to the kind of protective groups to be eliminated. When the elimination reaction is conducted with an acid, it can be carried out in the presence or absence of a solvent. Suitable solvents may include an organic solvent, water or a mixed solvent thereof. When trifluoroacetic acid is used, the elimination reaction may preferably be carried out in the presence of anisole.

The hydrolysis using hydrazine is commonly applied for eliminating the protective groups, for example, succinyl or phthaloyl.

The hydrolysis using a base is preferably applied for elimination of an acyl group. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

Among the protective group, the acyl group can generally be eliminated by hydrolysis as mentioned above or by the other conventional hydrolysis. In case that the acyl group is halo(lower)alkoxycarbonyl or 8-quniolyloxycarbonyl, they are eliminated by treating with a heavy metal such as copper, zinc or the like.

The reductive elimination is generally applied for eliminating the protective group, for example, halo(lower or higher)alkoxycarbonyl (e.g. trichloroethoxycarbonyl, etc.), substituted or unsubstituted ar(lower)alkoxycarbonyl (e.g. benzyloxycarbonyl, etc.) etc. Suitable reduction may include, for example, reduction with an alkali metal borohydride (e.g. sodium borohydride, etc.), reduction using a combination of a metal (e.g. zinc, zinc amalgam, etc.) and an organic or inorganic acid (e.g. acetic acid, propionic acid, hydrochloric acid, etc.), catalytic reduction, and the like.

Suitable iminohalogenating agents used in a method as mentioned above may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out at ambient temperature or under cooling. Suitable iminoetherifying agents reacted with thus obtained reaction product may include an alcohol, metal alkoxide and the like. Suitable alcohol may include alkanol (e.g. methanol, ethanol, propanol, isopropanol, butanol, tert-butanol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like.

The reaction temperature is not critical, and the reaction is usually carried out under cooling at ambient temperature or under warming.

PROCESS 4

The object compound (Ie) or a salt thereof can be prepared by subjecting the compound (If) or a salt thereof to the elimination reaction of the amino protective group.

Suitable salts of the compound (If) can be referred to the ones as exemplified for the compound (I).

The present elimination reaction is carried out substantially in the same manner as illustrated in Process 3.

The processes for preparing the starting compounds (III) are explained in detail as follows.

Suitable reactive derivative at the mercapto group of the compound (V), (IV), (IIIa), (IIIb), (IIIc), (IIId), (IIIe) and (IIIf) can be referred to the ones as exemplified for the compound (III).

Suitable salts of the compound (IV), (IIIa), (IIIb), (IIIc) and (IIIe) are each referred to the ones as exemplified for the compound (VI).

Suitable salts of the compound (IIId), (IX) and (VIa) are each referred to the ones as exemplified for the compound (I).

Suitable salts of the compound (VIII) and (X) include an inorganic acid salt (e.g., hydrochloride, hydrobromide, sulfate, etc.), an organic acid salt (e.g., acetate, p-toluenesulfonate, etc.) and the like.

PROCESS A (V)→(IV) 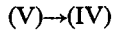

The compound (IV) or its reactive derivative at the mercapto group or a salt thereof can be prepared by reacting the compound (V) or its reactive derivative at the mercapto group with the compound (VII) or its ester.

Suitable esters of the compound (VII) are referred to the ones exemplified for the ester moiety of the esterified carboxy groups represented by $R^2$ and $R^3$.

The present reaction may be carried out in the presence of a base such as alkyl alkali metal (e.g. n-butyllithium, etc.), alkali metal acetate (e.g. sodium acetate, etc.), alkali metal alkoxide (e.g. sodium methoxide, potassium tert-butoxide, etc.), alkali metal hydride (e.g. sodium hydride, etc.), alkali metal hydroxide, alkaline earth metal hydroxide or the like.

The present reaction is usually carried out in a solvent such as tetrahydrofuran or any other solvents which do not adversely affect the reaction.

The reaction temperature is not critical and the reaction is preferably carried out under cooling or at ambient temperature.

PROCESS B (i): optional process

The compound (IV) or its reactive derivative at the mercapto group or a salt thereof wherein $R^3$ is a protected carboxy group may, if desired, be converted into its free form by elimination of the carboxy protective group, prior to;
  (ii) introduction of the substituent: =N—OR$^4$; or
  (iii) conversion of the —CO— group to the —CH(OH) group.

In the present elimination reaction, conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base (e.g. sodium hydroxide, etc.) or an acid (e.g. hydrochloric acid, formic acid, etc.).

The present reaction is usually carried out in a solvent such as alcohol (e.g. methanol, etc.) or any other solvents which do not adversely affect the reaction.

The reaction temperature is not critical and the reaction is preferably carried out under cooling, at ambient temperature or under warming.

(ii) (IV)+(VIII)→(IIIa) 

The compound (IIIa) or its reactive derivative at the mercapto group or a salt thereof can be prepared by reacting the compound (IV) or its reactive derivative at the mercapto group or a salt thereof with the compound (VIII) or a salt thereof.

The reaction is usually carried out in a conventional solvent such as water, alcohol (e.g., methanol, ethanol, etc.), a mixture thereof or any other ones which do not adversely influence the reaction.

When the compound (VIII) is used in its salt form, the reaction is preferably carried out in the presence of an organic or an inorganic base as exemplified before.

The reaction temperature is not critical, and the reaction is usually carried out from cooling to heating.

(iii) (IV)→(IIIb) 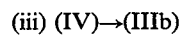

(i) The compound (IIIb) or its reactive derivative at the mercapto group or a salt thereof can be prepared by reducing the compound (IV) or its reactive derivative at the mercapto group or a salt thereof.

The present reduction can be carried out by a conventional method which is applied to the reduction of the —CO— group to the corresponding —CH(OH)— group, for example, by using a combination of a metal (e.g. zinc, etc.) and an acid (e.g. formic acid, acetic acid, hydrochloric acid, etc.) or a base (e.g. sodium hydroxide, etc.), alkali metal borohydride (e.g. lithium borohydride, etc.), metal amalgam (e.g. aluminum amalgam, etc.) or the like.

The present reaction is preferably carried out in a solvent such as alcohol (e.g. ethanol, etc.) or any other solvents which do not adversely affect the reaction.

The reaction temperature is not critical and the reaction is preferably carried out under cooling, at ambient temperature or under warming.

PROCESS C (i) (IIIa)→(IIId) 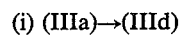

The compound (IIId) or its reactive derivative at the mercapto group or a salt thereof can be prepared by reducing the compound (IIIa) or its reactive derivative at the mercapto group or a salt thereof.

The present reduction can be carried out by the methods explained in Process B (iii), among which the method of using a combination of a metal (e.g. zinc, etc.) and an acid (e.g. formic acid, hydrochloric acid, etc.) are preferred.

(ii) (IIId)→(IIIc) 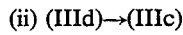

(a) The compound (IIIc) or its reactive derivative at the mercapto group or a salt thereof can be prepared by subjecting the compound (IIId) or its reactive derivative at the mercapto group or a salt thereof to the introduction reaction of the amino protective group.

The present introduction reaction can be carried out by reacting the compound (IIId) or its reactive derivative at the mercapto group or a salt thereof with an acylating agent. Suitable acylating agent may include (a) R$^9$—OH (VI) (wherein R$^9$ is acyl as defined above) or its reactive derivatives or a salt thereof as explained in Process 2.

(b) an introducing agent of lower alkoxycarbonyl grop, for example, 2-(lower)alkoxycarbonyloxyimino-2cyanoacetamide (e.g., 2-ethoxycarbonyloxyimino-2-cyanoacetamide, etc.), di(lower)alkyl 2-(lower)alkoxycarbonyloxyiminomalonate (e.g. diethyl 2-tert-butoxycarbonyloxyiminomalonate, etc.), lower alkyl 2-(lower)alkoxycarbonyloxyimino-2-cyanoacetate (e.g. ethyl 2-isobutoxycarbonyloxyimino-2-cyanoacetate, etc.), lower alkyl 2-(lower)alkoxycarbonyloxyiminoacetoacetate (e.g. ethyl 2-tert-butoxycarbonyloxyiminoacetoacetate, etc.), lower alkoxycarbonyloxyimino-2-phenylacetonitrile (e.g. tert-butoxycarbonyloxyimino-2-phenylacetonitrile, etc.) or the like, and the like.

The substantially same reaction conditions as set out in Process 2 can be applied in this reaction.

PROCESS D (IIIf)→(IIIe)

The compound (IIIe) or its reactive derivative at the mercapto group or a salt thereof can be prepared by subjecting the compound (IIIf) or its reactive derivative at the mercapto group to the reaction to introduce a carboxy group; whereafter, if necessary, the introduction of a carboxy protective group is carried out.

The present reaction can be carried out by a conventional method which is applied for the introduction of a carboxy group to the alkenyl group, for example by reacting the compound (IIIf) with dry ice or carbon dioxide, or the like.

The present reaction is usually carried out in the presence of a base as exemplified in Process A.

The present reaction is usually carried out in a solvent such as tetrahydrofuran, hexan or any other solvents which do not adversely affect the reaction. The reaction temperature is not critical and the reaction is preferably carried out under cooling or at ambient temperature.

PROCESS E (i) (XI)→(X)

The compound (X) or a salt thereof can be prepared by subjecting a compound (XI) to elimination reaction of the amino protective group.

This elimination reaction of the amino protective group of the compound (XI) can be carried out in a similar manner to that of aforementioned Process 3.

Suitable solvents include water, ethanol, chloroform, diethyl ether and the like. The reaction temperature is not critical and the reaction is usually carried out under warming or heating.

(ii) (X)+(IX)→(VIa)

The compound (VIa) or a salt thereof can be prepared by reacting a compound (X) or a salt thereof with a compound (IX) or a salt thereof.

The reaction is usually carried out in a conventional solvent such as water, alcohol (e.g. methanol, ethanol, etc.), a mixture thereof or any other ones which do not adversely influence the reaction.

When the compound (X) is used in its salt form, the reaction is preferably carried out in the presence of an organic or an inorganic base as exemplified before.

The reaction temperature is not critical, and the reaction is usually carried out from cooling to heating.

In the present reaction, a syn isomer of the compound (VIa) can be obtained preferably by conducting the present reaction under around neutral conditions.

The present invention includes, within its scope, the cases that protected amino and/or protected carboxy and/or protected hydroxy group(s) are transformed into the corresponding free amino and/or carboxy and/or hydroxy group(s) according to the reaction conditions and kinds of the protective groups in the course of the aforementioned reactions and/or in post-treatment of the reactions in Processes 1 to 4 and A to E.

In the aforementioned reactions and/or the post-treating of the reactions in Processes 1 to 4 and A to E of the present invention, the aforementioned geometrical isomer and/or tautomeric isomer may occasionally be transformed into the other geometrical isomer and/or tautomeric isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable or oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now, in order to show the utility of the object compounds (I), test data on anti-microbial activity of a representative compound of the present invention are shown below.

TEST COMPOUND (1) 7-[2-Methoxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position).

(2) 7-[2-(2-Cyclopenten-1-yl)oxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position).

(3) 7-[2-Methoxyimino-2-(2-aminothiazol-4-yl)-acetamido]-3-[1-(2-carboxy-2-aminoethyl)-1H-tetrazol-5-yl]thiomethyl-3-cephem-4-carboxylic acid (syn isomer: in the 7-position).

TEST METHOD

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

| | Test result | | |
|---|---|---|---|
| | M.I.C. (μg/ml) | | |
| Test Microorganism | Compound (1) | Compound (2) | Compound (3) |
| Klebsiella pneumoniae 20 | 0.20 | 0.39 | 0.39 |
| Proteus mirabilis 1 | 0.05 | 0.39 | 0.20 |
| Proteus vulgaris 2 | 0.05 | 0.39 | 0.10 |

The following preparations and examples are given for the purpose of illustrating the present invention.

PREPARATION 1

A solution of 1-methyl-1H-tetrazole-5-thiol (23 g) in dry tetrahydrofuran (80 ml) was added over 20 minutes with stirring under dry nitrogen atmosphere to a n-butyllithium (250 ml, 15% in hexane) solution in dry tetrahydrofuran (250 ml) precooled to −15° to −10° C. After stirring at the same temperature for 40 minutes, the mixture was cooled to −60°±5° C. and thereto was added dropwise a solution of diethyl oxalate (28.95 g) in dry tetrahydrofuran (80 ml) over 30 min. The reaction mixture was stirred at −60°±5° C. for 1.5 hours. 10% Aqueous hydrochloric acid (72 ml) was added with stirring and the separated aqueous layer (pH 7.5) was adjusted to pH 2.5 with 10% hydrochloric acid and extracted with ethyl acetate (200 ml×3). The combined extracts were dried over magnesium sulfate and evaporated to give oily residue of 1-ethoxalylmethyl-1H-tetrazole-5-thiol (34.3 g).

I.R. (Nujol): 1730 cm$^{-1}$.

N.M.R. (CDCl$_3$, δ): 1.43 (3H, t, J=7 Hz); 4.46 (2H, q, J=7 Hz); 5.67 (2H, s).

PREPARATION 2

To a solution of 1-ethoxalylmethyl-1H-tetrazole-5-thiol (18.6 g) in methanol (186 ml) was added 1N aqueous solution of sodium hydroxide (172 ml) at room temperature and the mixture was stirred for 40 minutes. After adjusting to pH 7.5 with 10% hydrochloric acid, the solution was evaporated in vacuo to remove methanol and the remained aqueous solution was washed with ethyl acetate (100 ml). The aqueous solution was adjusted to pH 4.0 and washed again with ethyl acetate to remove impurities. The aqueous solution was adjusted to pH 2.5, and extracted with ethyl acetate, dried over magnesium sulfate and evaporated to give pale yellow powder of 1-oxalomethyl-1H-tetrazole-5-thiol (9.7 g), mp 140° to 150° C. (dec.).

I.R. (Nujol): 1750, 1710 cm$^{-1}$.

N.M.R. (DMSO-d$_6$, δ): 5.71 (2H, s).

PREPARATION 3

A solution of 1-oxalomethyl-1H-tetrazole-5-thiol (10.0 g) and hydroxylamine hydrochloride (4.8 g) in water (100 ml) was adjusted to pH 6.0 with 2N aqueous solution of sodium hydroxide and stirred at room temperature for 3.5 hours. The solution was acidified with 10% hydrochloric acid to pH 2.0, extracted with a mixture of tetrahydrofuran and ethyl acetate (1:1). The extract was washed with a saturated aqueous solution of sodium chloride, dried over magnesium sulfate and evaporated to give 1-(2-carboxy-2-hydroxyiminoethyl)-1H-tetrazole-5-thiol (5.61 g).

N.M.R. (DMSO-d$_6$, δ): 5.19 (2H, s).

PREPARATION 4

A solution of 1-oxalomethyl-1H-tetrazole-5-thiol (1.09 g) and methoxyamine hydrochloride (0.47 g) in water (15 ml) was adjusted to pH 6.5 with sodium bicarbonate and stirred at room temperature for 2 hours. After washing with ethyl acetate, the aqueous solution was adjusted to pH 1.8 with 10% hydrochloric acid, extracted with ethyl acetate, dried over magnesium sulfate and evaporated to give 1-(2-carboxy-2-methoxyiminoethyl)-1H-tetrazole-5-thiol (1.05 g), mp 84° to 86° C.

I.R. (Nujol): 1685 cm$^{-1}$.

N.M.R. (DMSO-d$_6$, δ): 3.97 (3H, s), 5.17 (2H, s).

PREPARATION 5

The following compound was prepared according to the similar manners to those of Preparation 1 to 4. 1-(2-Carboxy-2-allyloxyiminoethyl)-1H-tetrazole-5-thiol.

I.R. (Nujol): 1700 cm$^{-1}$.

N.M.R. (DMSO-d$_6$, δ): 4.58 (2H, m), 4.98–5.33 (4H, m), 5.58–6.07 (1H, m).

PREPARATION 6

1-Oxalomethyl-1H-tetrazole-5-thiol (0.94 g) was dissolved in aqueous 60% ethanol (15 ml) containing sodium hydroxide (1.4 g) and to this solution was added portionwise zinc powder (0.98 g). The mixture was stirred at room temperature for 3.5 hours. After removal of zinc powder by filtration, ethanol was removed under reduced pressure and the remained aqueous solution was adjusted to pH 2.0 with 10% hydrochloric acid. Extraction with ethyl acetate, drying over magnesium sulfate and evaporation gave an oil which was triturated with a mixture of diisopropyl ether and n-hexane (1:1). The crystals were filtered and washed with a mixture of diisopropyl ether and n-hexane (1:1) to give 1-(2-carboxy-2-hydroxyethyl)-1H-tetrazole-5-thiol (0.40 g), mp 143° to 146° C., I.R. (Nujol): 3320, 3180, 1715 cm$^{-1}$.

N.M.R. (DMSO-d$_6$, δ): 4.17–4.57 (3H, m).

PREPARATION 7

A mixture of 1-(2-carboxy-2-hydroxyiminoethyl)-1H-tetrazole-5-thiol (19.3 g), 50% formic acid (255 ml), zinc powder (22.3 g) in ethanol (230 ml) was stirred for 5 hours at room temperature. After the addition of trifluoroacetic acid (100 ml), the mixture was stirred for 5 minutes and filtered. The filtrate was evaporated under reduced pressure. The residue was adjusted to pH 13.0 with 4N aqueous solution of sodium hydroxide and then filtered. The filtrate containing disodium 1-(2-carboxylate-2-aminoethyl)-1H-tetrazole-5-thiolate was adjusted to pH 6.0 and thereto were added dioxane (300 ml), 2-tert-butoxycarbonyloxyimino-2-phenylacetonitrile (35.1 g) and triethylamine (26.2 g). The resulting mixture was stirred overnight at room temperature. The reaction mixture was adjusted to pH 7.0 and washed with ethyl acetate. The washed layer was adjusted to pH 2.0 with phosphoric acid and then extracted with ethyl acetate. The extract was washed with a saturated aqueous solution of sodium chloride, dried over magnesium sulfate and evaporated. The residue was pulverized in diisopropyl ether to give 1-(2-carboxy-2-tert-butoxycarboxamidoethyl)-1H-tetrazole-5-thiol (21.2 g).

I.R. (Nujol): 3400, 1718, 1690 cm$^{-1}$.

N.M.R. (DMSO-$d_6$, δ): 1.34 (9H, s), 4.33–4.80 (3H, m), 7.27 (1H, broad s).

PREPARATION 8

15% solution of n-butyl lithium in hexane (371 ml) was dissolved in dry tetrahydrofuran (150 ml) and cooled to −20° C. To the solution was added dropwise a solution of 1-allyl-1H-tetrazole-5-thiol (38.7 g) in tetrahydrofuran (220 ml) with stirring under a stream of nitrogen gas during a period of 30 minutes. After the addition of solid carbon dioxide, the mixture was stirred for 30 minutes at −10° C. To the mixture was added water (275 ml) and then the resulting mixture was stirred. The aqueous layer was separated adjusted to pH 4.5, washed with ethyl acetate, adjusted to pH 3.8 to 4.0 and extracted with ethyl acetate. The extract was washed with a saturated aqueous solution of sodium chloride, dried over magnesium sulfate and then evaporated. The residue was washed with diisopropyl ether to give an oil of 1-(3-carboxy-1-propenyl)-1H-tetrazole-5-thiol (5.5 g).

I.R. (Nujol): 1700 cm$^{-1}$.

N.M.R. (DMSO-$d_6$, δ): 3.57 (2H, m), 6.00 (1H, m); 7.05 (1H, m).

The remaining aqueous layer was adjusted to pH 1.5 and extracted with ethyl acetate. The extract was washed with a saturated aqueous solution of sodium chloride, dried over magnesium sulfate and evaporated to give 1-(1-carboxyallyl)-1H-tetrazole-5-thiol (21.3 g).

I.R. (Film): 1710, 1620 cm$^{-1}$.

N.M.R. (DMSO-$d_6$, δ): 5.30–5.70 (2H, m), 5.90–6.67 (2H, m).

PREPARATION 9

To a solution of 2-(2-formamidothiazol-4-yl)-glyoxylic acid (30 g) and sodium bicarbonate (12.6 g) in water (1300 ml) was added allyloxyamine hydrochloride (19.8 g), and the mixture was stirred for 7 hours at ambient temperature at pH 6. To the reaction mixture was added ethyl acetate (500 ml). After the mixture was adjusted to pH 1.9 with 10% hydrochloric acid, the ethyl acetate layer was separated. The ethyl acetate layer was washed with an aqueous solution of sodium chloride, dried over magnesium sulfate and then the solvent was distilled off. The residue was pulverized in diisopropyl ether, collected by filtration and then dried to give 2-allyloxyimino-2-(2-formamidothiazol-4-yl)acetic acid (syn isomer) (25.3 g).

I.R. (Nujol): 3110, 1730, 1660, 1540 cm$^{-1}$.

N.M.R. ($d_6$-DMSO, δ): 4.70 (2H, m), 5.13–5.60. (2H, m), 5.73–6.27 (1H, m), 7.57 (1H, s), 8.35 (1H, s).

PREPARATION 10

(1) Ethyl 2-(2-propynyloxyimino)-3-oxobutyrate (syn isomer) (71.2 g) was obtained by reacting ethyl 2-hydroxyimino-3-oxobutyrate (syn isomer) (56.7 g) with 2-propynyl bromide (43 g) in the presence of potassium carbonate (72.3 g) and N,N-dimethylformamide (280 ml).

I.R. (Film): 3280, 3220, 2120, 1735, 1670 cm$^{-1}$.

(2) Ethyl 2-(2-propynyloxyimino)-3-oxo-4-chlorobutyrate (syn isomer) (61.6 g) was obtained by reacting ethyl 2-(2-propynyloxyimino)-3-oxobutyrate (syn isomer) (71.2 g) with sulfuryl chloride (50.2 g) in acetic acid (81 ml).

I.R. (Film): 3300, 2130, 1745, 1720, 1675 cm$^{-1}$.

(3) Ethyl 2-(2-propynyloxyimino)-2-(2-aminothiazol-4-yl)acetate (syn isomer) (35.6 g) was obtained by reacting ethyl 2-(2-propynyloxyimino)-3-oxo-4-chlorobutyrate (syn isomer) (61 g) with thiourea (20 g) in the presence of sodium acetate trihydrate (35.8 g), water (150 ml) and ethanol (180 ml).

I.R. (Nujol): 3290, 2220, 1729 cm$^{-1}$.

(4) 2-(2-Propynyloxyimino)-2-(2-aminothiazol-4-yl)acetic acid (syn isomer) (1.924 g) was obtained by hydrolyzing ethyl 2-(2-propynyloxyimino)-2-(2-aminothiazol-4-yl)acetate (syn isomer) (2.8 g) in the presence of 1N aqueous solution of sodium hydroxide (22.17 ml), methanol (23 ml) and tetrahydrofuran (20 ml).

I.R. (Nujol): 2190, 1740 cm$^{-1}$.

(5) 2-(2-Propynyloxyimino)-2-[2-(2,2,2-trifluoroacetamido)-thiazol-4-yl]acetic acid (syn isomer) (11.4 g) was obtained by reacting 2-(2-propynyloxyimino)-2-(2-aminothiazol-4-yl)-acetic acid (syn isomer) (10.0 g) with 2,2,2-trifluoroacetic anhydride (22.5 g) in the presence of bis(trimethylsilyl)acetamide (22.3 g) and dry ethyl acetate (100 ml).

I.R. (Nujol): 3280, 3130, 2140, 1710, 1575, 1360, 1260, 1210, 1165, 1075, 1020, 980, 750 cm$^{-1}$.

N.M.R. (DMSO-$d_6$, δ): 3.53 (1H, t, J=2 Hz); 4.83 (2H, d, J=2 Hz); 7.73 (1H, s).

PREPARATION 11

(1) The following compounds were obtained according to a similar manner to that of Preparation 10(1).

(i) Ethyl 2-cyclopentyloxyimino-3-oxobutyrate (syn isomer), oil.

I.R. (Film): 1740, 1670, 1495, 1430 cm$^{-1}$.

N.M.R. (CCl$_4$, δ): 1.32 (3H, t, J=7 Hz), 1.4–2.2 (8H, m), 2.33 (3H, s), 4.27 (2H, q, J=7 Hz), 4.87 (1H, m).

(ii) Ethyl 2-benzyloxyimino-3-oxobutyrate (syn isomer).

(iii) Ethyl 2-(4-fluorobenzyloxyimino)-3-oxobutyrate (syn isomer).

I.R. $\nu_{max}^{Film}$: 3000, 2940, 1730, 1690, 1600 cm$^{-1}$.

N.M.R. δ(DMSO-$d_6$, ppm): 1.21 (3H, t, J=7.0 Hz), 2.34 (3H, s), 4.26 (2H, q, J=7.0 Hz), 5.32 (2H, s), 6.97–7.73 (4H, m).

(2) The following compounds were obtained according to a similar manner to that of Preparation 10(2).

(i) Ethyl 2-cyclopentyloxyimino-3-oxo-4-chlorobutyrate (syn isomer), oil.

I.R. (Film): 1750, 1735, 1465, 1435 cm$^{-1}$.

N.M.R. (CCl$_4$, δ): 1.33 (3H, t, J=7 Hz), 1.3–2.4 (8H, m), 4.28 (2H, q, J=7 Hz), 4.46 (2H, s), 4.86 (1H, m).

(ii) Ethyl 2-benzyloxyimino-3-oxo-4-chlorobutyrate (syn isomer).

(iii) Ethyl 2-(4-fluorobenzyloxyimino)-3-oxo-4-chlorobutyrate (syn isomer).

I.R. $\nu_{max}^{Film}$: 1720, 1600 cm$^{-1}$.

N.M.R. δ(DMSO-$d_6$, ppm): 1.20 (3H, t, J=7.0 Hz), 4.28 (2H, q, J=7.0 Hz), 4.87 (2H, s), 5.36 (2H, s), 7.00–7.75 (4H, m).

(3) The following compounds were obtained according to a similar manner to that of Preparation 10(3).

(i) Ethyl 2-cyclopentyloxyimino-2-(2-aminothiazol-4-yl)acetate (syn isomer), mp 134° to 136° C.

I.R. (Nujol): 3490, 3450, 3250, 3120, 1735, 1540, 1460 cm$^{-1}$.

N.M.R. (DMSO-d$_6$, δ): 1.25 (3H, t, J=7 Hz), 1.62 (8H, broad s), 4.27 (2H, q, J=7 Hz); 4.70 (1H, m); 6.85 (1H, s), 7.20 (2H, s).

(ii) Ethyl-2-benzyloxyimino-2-(2-aminothiazol-4-yl)-acetate (syn isomer).

I.R. $\nu_{max}^{Nujol}$: 3440, 3240, 3100, 1730, 1680 cm$^{-1}$.

(iii) Ethyl 2-(4-fluorobenzyloxyimino)-2-(2-aminothiazol-4-yl)acetate (syn isomer).

I.R. $\nu_{max}^{Nujol}$: 3450, 3150, 3100, 1710, 1620 cm$^{-1}$.

N.M.R. δ(DMSO-d$_6$, ppm): 1.23 (3H, t, J=7.0 Hz), 4.30 (2H, q, J=7.0 Hz), 5.15 (2H, s), 6.90 (1H, s), 6.95–7.60 (4H, m).

(4) The following compounds were obtained according to a similar manner to that of Preparation 10(4).

(i) 2-Cyclopentyloxyimino-2-(2-aminothiazol-4-yl)-acetic acid (syn isomer), mp 186° C. (dec.).

I.R. (Nujol): 3330, 3120, 1635, 1450 cm$^{-1}$.

N.M.R. (DMSO-d$_6$, δ): 1.1–2.2 (8H, m), 4.68 (1H, m), 6.81 (1H, s), 7.18 (2H, broad s).

(ii) 2-Benzyloxyimino-2-(2-aminoethiazol-4-yl)acetic acid (syn isomer).

I.R. $\nu_{max}^{Nujol}$: 3330, 3200, 3100, 1660, 1590 cm$^{-1}$.

N.M.R. δ(DMSO-d$_6$, ppm): 5.20 (2H, s); 6.90 (1H, s); 7.40 (5H, s).

(iii) 2-(4-Fluorobenzyloxyimino)-2-(2-aminothiazol-4-yl)acetic acid (syn isomer).

I.R. $\nu_{max}^{Nujol}$: 3650, 3450, 3300, 3150, 1630 cm$^{-1}$.

N.M.R. δ(DMSO-d$_6$, ppm): 5.16 (2H, s); 6.88 (1H, s); 7.04–7.66 (4H, m).

(5) The following compounds were obtained according to a similar manner to that of Preparation 10(5).

(i) 2-Cyclopentyloxyimino-2-[2-(2,2,2-trifluoroacetamido)thiazol-4-yl]acetic acid (syn isomer).

I.R. (Nujol): 3200, 3130, 1720, 1590, 1580 cm$^{-1}$.

N.M.R. (DMSO-d$_6$, δ): 1.34–2.22 (8H, m), 4.81 (1H, m), 7.71 (1H, s).

(ii) 2-Benzyloxyimino-2-[2-(2,2,2-trifluoroacetamido)-thiazol-4-yl]acetic acid (syn isomer).

I.R. (Nujol): 3130, 1730, 1600, 1580 cm$^{-1}$.

N.M.R. (DMSO-d$_6$, δ): 5.23 (2H, s), 7.36 (5H, s); 7.67 (1H, s).

(iii) 2-(4-Fluorobenzyloxyimino)-2-[2-(2,2,2-trifluoroacetamido)thiazol-4-yl]acetic acid (syn isomer), mp 180°–182° C.

I.R. $\nu_{max}^{Nujol}$: 3200, 3150, 1730 cm$^{-1}$.

N.M.R. δ(DMSO-d$_6$, ppm): 5.25 (2H, s); 7.02–7.60 (4H, m), 7.72 (1H, s).

PREPARATION 12

A mixture of 3-chlorocyclopentene (36.9 g), N-hydroxyphthalimide (58.2 g) and triethylamine (53.9 g) in acetonitrile (370 ml) was refluxed for 2 hours. The reaction mixture was poured into ice-water. The precipitated crystals were collected by filtration, washed with water and dried over phosphorus pentoxide to give N-(2-cyclopenten-1-yl)oxyphthalimide (56.5 g).

I.R. (Nujol): 1780, 1730, 1610 cm$^{-1}$. N.M.R. (DMSO-d$_6$, δ): 1.98–2.9 (4H, m), 5.42 (1H, s), 6.00 (1H, m), 6.28 (1H, m), 7.92 (4H, s).

PREPARATION 13

A mixture of N-phenoxyphthalimide (5.5 g) and hydrazine hydrate (1.15 g) in ethanol (120 ml) was stirred for 1.5 hours at 75° to 80° C. After the addition of conc. hydrochloric acid (4 ml) and water (40 ml) to the reaction mixture under ice-cooling, the resulting mixture was filtered and the filtrate was evaporated. The remaining mixture containing phenoxyamine hydrochloride was adjusted to pH 7.0 with 10% aqueous solution of sodium hydroxide and thereto were added 2-(2-formamidothiazol-4-yl)glyoxylic acid (3.54 g). The resulting mixture was adjusted to pH 5.0 to 5.5 with 10% hydrochloric acid and stirred for 2 hours at room temperature. The reaction mixture was evaporated under reduced pressure and to the residue was added ethyl acetate. The resulting mixture was adjusted to pH 7.0 with a saturated aqueous solution of sodium bicarbonate. The aqueous layer was separated, adjusted to pH 2.0 with 10% hydrochloric acid and extracted with ethyl acetate. The extract was washed with a saturated aqueous solution of sodium chloride. The solution was dried over magnesium sulfate and concentrated under reduced pressure. The residue was pulverized in diethyl ether to give 2-phenoxyimino-2-(2-formamidothiazol-4-yl)acetic acid (syn isomer).

I.R. (Nujol): 3200, 1700, 1690, 1590, 1560 cm$^{-1}$.

N.M.R. (DMSO-d$_6$, δ): 12.60 (1H, broad s); 8.58 (1H, s), 7.85 (1H, s), 7.73–6.67 (5H, m).

PREPARATION 14

The following compound was obtained according to a similar manner to that of Preparation 13. 2-(2-Cyclopenten-1-yl)oxyimino-2-(2-formamidothiazol-4-yl)acetic acid (syn isomer).

I.R. (Nujol): 3200, 1740, 1710, 1600, 1560 cm$^{-1}$.

N.M.R. (DMSO-d$_6$, δ): 1.52–2.67 (4H, m), 5.45 (1H, m), 6.00 (1H, m); 6.28 (1H, m), 7.67 (1H, s), 8.73 (1H, s), 13.0 (1H, broad s).

EXAMPLE 1

To a suspension of 7-aminocephalosporanic acid (12.1 g) and 1-(2-carboxy-2-hydroxyiminoethyl)-1H-tetrazole-5-thiol (9.0 g) in dry acetonitril (60 ml) was added boron trifluoride etherate (25.1 g) and the resulting solution was stirred at 50° for 50 minutes. Water (60 ml) as added and the solution was adjusted to pH 3.5 with conc. aqueous ammonia to give precipitates which were filtered, washed successively with water and acetone, and air-dried to give 7-amino-3-[1-(2-carboxy-2-hydroxyiminoethyl)-1H-tetrazol-5-yl]-thiomethyl-3-cephem-4-carboxylic acid (13.92 g).

I.R. (Nujol): 3160, 1800, 1620 cm$^{-1}$.

N.M.R. (DMSO-d$_6$, δ): 3.62 (2H, m), 4.30 (2H, q, J=14.0 Hz), 4.77 (1H, d, J=5.0 Hz), 4.96 (1H, d, J=5.0 Hz), 5.24 (2H, broad s).

EXAMPLE 2

To a suspension of 7-aminocephalosporanic acid (0.99 g) and 1-(2-carboxy-2-methoxyiminoethyl)-1H-tetrazole-5-thiol (0.95 g) in dry acetonitrile (10 ml) was added boron trifluoride etherate (1.55 g) and the resulting solution was stirred at 50° C. for 2 hours. Water (10 ml) was added to the reaction mixture and the solution was adjusted to pH 3.5 with conc. aqueous ammonia under ice-cooling to give precipitates which were filtered, washed with water and dried to give 7-amino-3-[1-(2-carboxy-2-methoxyiminoethyl)-1H-tetrazol-5- yl]thiomethyl-3-cephem-4-carboxylic acid (1.0 g), mp 170° to 180° C. (dec.).

I.R. (Nujol): 1800, 1705, 1615 cm$^{-1}$.

N.M.R. (DMSO-d$_6$, δ): 3.63 (2H, ABq, J=18 Hz); 3.96 (3H, s), 4.30 (2H, ABq, J=14 Hz); 4.78 (1H, d, J=5 Hz), 4.97 (1H, d, J=5 Hz); 5.27 (2H, s).

EXAMPLE 3

To a suspension of 7-[2-methoxyimino-2-(2-aminothiazol-4-yl)acetamido]cephalosporanic acid (syn isomer) (1.14 g) and 1-(2-carboxy-2-methoxyiminoethyl)-1H-tetrazole-5-thiol (0.81 g) in water (20 ml) was added sodium bicarbonate and the solution was adjusted to pH 6.5 and then stirred for 5 hours at 60° C. After cooling at 10° to 15° C., the solution was adjusted to pH 2.5 with 10% hydrochloric acid. The precipitates were collected by filtration, washed with water and then dried to give 7-[2-methoxyimino-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position).

I.R. (Nujol): 3270, 1770, 1645 cm$^{-1}$.

EXAMPLE 4

The following compounds were prepared according to the similar manners to those of Examples 1 to 3.

(1) 7-amino-3-[1-(2-carboxy-2-allyloxyiminoethyl)-1H-tetrazol-5-yl]thiomethyl-3-cephem-4-carboxylic acid, mp 165° to 170° C. (dec.).

I.R. (Nujol): 1790, 1695, 1605 cm$^{-1}$.

N.M.R. (DMSO-d$_6$, δ): 3.60 (2H, ABq, J=18 Hz); 4.30 (2H, ABq, J=14 Hz), 4.67–5.10 (6H, m), 5.29 (2H, s), 5.60–6.23 (1H, m).

(2) 7-amino-3-[1-(2-carboxy-2-hydroxyethyl)-1H-tetrazol-5-yl]thiomethyl-3-cephem-4-carboxylic acid.

I.R. (Nujol): 1795, 1725, 1615 cm$^{-1}$.

N.M.R. (DMSO-d$_6$, δ): 3.67 (2H, m), 4.23–4.73 (5H, m), 4.91 (1H, d, J=5 Hz), 5.10 (1H, d, J=5 Hz).

(3) 7-[2-Methoxyimino-2-(2-formamidothiazol-yl)acetamido]-3-[1-(2-carboxy-2-hydroxyiminoethyl)-1H-tetrazol-5-yl]thiomethyl-3-cephem-4-carboxylic acid (syn isomer: in the 7-position).

I.R. (Nujol): 1760, 1650 cm$^{-1}$.

(4) 7-[2-Cyclopentyloxyimino-2-{2-(2,2,2-trifluoroacetamido)thiazol-4-yl}acetamido]-3-[1-(2-carboxy-2-hydroxyiminoethyl)-1H-tetrazol-5-yl]thiomethyl-3-cephem-4-carboxylic acid (syn isomer: in the 7-position).

I.R. (Nujol): 3150, 1770, 1710, 1660 cm$^{-1}$.

(5) 7-[2-(2-Cyclopenten-1-yl)oxyimino-2-(2-formamidothiazol-4-yl)acetamido]-3-[1-(2-carboxy-2-hydroxyiminoethyl)-1H-tetrazol-5-yl]-thiomethyl-3-cephem-4-carboxylic acid (syn isomer: in the 7-position).

I.R. (Nujol): 3200, 1780, 1660 cm$^{-1}$.

(6) 7-[2-(4-Fluorobenzyl)oxyimino-2-{2-(2,2,2-trifluoroacetamido)thiazol-4-yl}acetamido]-3-[1-(2-carboxy-2-hydroxyiminoethyl)-1H-tetrazol-5-yl]thiomethyl-3-cephem-4-carboxylic acid (syn isomer: in the 7-position).

I.R. (Nujol): 3300, 1780, 1720, 1670 cm$^{-1}$.

(7) 7-[2-Methoxyimino-2-{2-(2,2,2-trifluoroacetamido)thiazol-4-yl}acetamido]-3-[1-(2-carboxy-2-methoxyiminoethyl)-1H-tetrazol-5-yl]thiomethyl-3-cephem-4-carboxylic acid (syn isomer: in the 7-position), mp 164° to 170° C. (dec.).

I.R. (Nujol): 1780, 1715, 1655 cm$^{-1}$.

(8) 7-[2-Isopropoxyimino-2-{2-(2,2,2-trifluoroacetamido)thiazol-4-yl}acetamido]-3-[1-(2-carboxy-2-methoxyiminoethyl)-1H-tetrazol-5-yl]thiomethyl-3-cephem-4-carboxylic acid (syn isomer: in the 7-position).

I.R. (Nujol): 1780, 1715 cm$^{-1}$.

(9) 7-[2-Allyloxyimino-2-(2-formamidothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position).

I.R. (Nujol): 1770, 1670 cm$^{-1}$.

(10) 7-[2-(2-Propynyloxyimino)-2-{2-(2,2,2-trifluoroacetamido)thiazol-4-yl}acetamido]-3-[1-(2-carboxy-2-methoxyiminoethyl)-1H-tetrazol-5-yl]thiomethyl-3-cephem-4-carboxylic acid (syn isomer: in the 7-position).

I.R. (Nujol): 3225, 2110, 1770, 1715, 1670 cm$^{-1}$z.

(11) 7-[2-(2-Cyclopenten-1-yl)oxyimino-2-(2-formamidothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position), mp 156° to 161° C. (dec.).

I.R. (Nujol): 1770, 1665 cm$^{-1}$.

(12) 7-[2-Benzyloxyimino-2-{2-(2,2,2-trifluoroacetamido)-thiazol-4-yl}acetamido]-3-[1-(2-carboxy-2-methoxyiminoethyl)-1H-tetrazol-5-yl]thiomethyl-3-cephem-4-carboxylic acid (syn isomer: in the 7-position), mp 165° to 170° C. (dec.).

I.R. (Nujol): 1775, 1710, 1650 cm$^{-1}$.

(13) 7-[2-(4-Fluorobenzyl)oxyimino-2-{2-(2,2,2-trifluoroacetamido)thiazol-4-yl}acetamido]-3-[1-(2-carboxy-2-methoxyiminoethyl)-1H-tetrazole-5-yl]thiomethyl-3-cephem-4-carboxylic acid (syn isomer: in the 7-position), mp 153° C. (dec.).

I.R. (Nujol): 1765, 1710, 1650 cm$^{-1}$.

(14) 7-[2-(2-Cyclopenten-1-yl)oxyimino-2-(2-formamidothiazol-4-yl)acetamido]-3-[1-(2-carboxy-2-allyloxyiminoethyl)-1H-tetrazol-5-yl]thiomethyl-3-cephem-4-carboxylic acid (syn isomer: in the 7-position), mp 150° to 160° C. (dec.).

I.R. (Nujol): 1775, 1670 cm$^{-1}$.

(15) 7-[2-Benzyloxyimino-2-{2-(2,2,2-trifluoroacetamido)-thiazol-4-yl}acetamido]-3-[1-(2-carboxy-2-allyloxyiminoethyl)-1H-tetrazol-5-yl]thiomethyl-3-cephem-4-carboxylic acid (syn isomer: in the 7-position).

I.R. (Nujol): 1775, 1710, 1650 cm$^{-1}$.

(16) 7-[2-(4-Fluorobenzyl)oxyimino-2-{2-(2,2,2-trifluoroacetamido)thiazol-4-yl}acetamido]-3-[1-(2-carboxy-2-hydroxyethyl)-1H-tetrazol-5-yl]-thiomethyl-3-cephem-4-carboxylic acid (syn isomer: in the 7-position), mp 90° to 100° C. (dec.).

I.R. (Nujol): 1770, 1710, 1650 cm$^{-1}$.

(17) 7-[2-Methoxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 169° to 173° C. (dec.).

I.R. (Nujol): 3300, 3200, 1770, 1660, 1630 cm$^{-1}$.

(18) 7-[2-Cyclopentyloxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 168° to 171° C. (dec.).

I.R. (Nujol): 3250, 3150, 1760, 1650 cm$^{-1}$.

(19) 7-[2-(2-Cyclopenten-1-yl)oxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 150° to 160° C. (dec.).

I.R. (Nujol): 3270, 3160, 1770, 1650 cm$^{-1}$.

(20) 7-[2-(4-Fluorobenzyl)oxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 160° to 163° C. (dec.).
I.R. (Nujol): 3200, 1770, 1640 cm$^{-1}$.

(21) 7-[2-Isopropoxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position), mp 140° to 150° C. (dec.).
I.R. (Nujol): 3260, 1770, 1660 cm$^{-1}$.

(22) 7-[2-Allyloxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position), mp 130° to 140° C. (dec.).
I.R. (Nujol): 3250, 1770, 1650 cm$^{-1}$.

(23) 7-[2-(2-Propynyloxyimino)-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position).
I.R. (Nujol): 3255, 1775, 1670, 1630 cm$^{-1}$.

(24) 7-[2-(2-Cyclopenten-1-yl)oxyimino-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position), mp 140° to 150° C. (dec.).
I.R. (Nujol): 3260, 1770, 1650 cm$^{-1}$.

(25) 7-[2-Benzyloxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position), mp 168° to 172° C. (dec.).
I.R. (Nujol): 3260, 1770, 1655 cm$^{-1}$.

(26) 7-[2-(4-Fluorobenzyl)oxyimino-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position), mp 130° to 140° C. (dec.).
I.R. (Nujol): 3270, 1770, 1625 cm$^{-1}$.

(27) 7-[2-(2-Cyclopenten-1-yl)oxyimino-2-(2-aminothiazol-4-yl)acetamido]-3-[1-(2-carboxy-2-allyloxyiminoethyl)-1H-tetrazol-5-yl]thiomethyl-3-cephem-4-carboxylic acid (syn isomer: in the 7-position), mp 140° to 150° C. (dec.).
I.R. (Nujol): 3270, 1770, 1660, 1630 cm$^{-1}$.

(28) 7-[2-Benzyloxyimino-2-(2-aminothiazol-4-yl)-acetamido]-3-[1-(2-carboxy-2-allyloxyiminoethyl)-1H-tetrazol-5-yl]thiomethyl-3-cephem-4-carboxylic acid (syn isomer: in the 7-position), mp 180° to 190° C. (dec.).
I.R. (Nujol): 3290, 1775, 1705, 1655 cm$^{-1}$.

(29) 7-[2-(4-Fluorobenzyl)oxyimino-2-(2-aminothiazol-4-yl)acetamido]-3-[1-(2-carboxy-2-hydroxyethyl)-1H-tetrazol-5-yl]thiomethyl-3-cephem-4-carboxylic acid (syn isomer: in the 7-position).
I.R. (Nujol): 3280, 1765, 1630 cm$^{-1}$.

(30) Disodium 7-amino-3-[1-(2-carboxylate-2-tert-butoxycarboxaminoethyl)-1H-tetrazol-5-yl]thiomethyl-3-cephem-4-carboxylate.
I.R. (Nujol): 1750, 1685, 1600 cm$^{-1}$.
N.M.R. (D$_2$O, δ): 1.30 (9H, s), 3.70 (2H, ABq, J=17 Hz), 4.05–4.87 (6H, m), 5.04 (1H, d, J=5 Hz).

(31) 7-[2-Methoxyimino-2-{2-(2,2,2-trifluoroacetamido)-thiazol-4-yl}acetamido]-3-[1-(2-carboxy-2-hydroxyethyl)-1H-tetrazol-5-yl]thiomethyl-3-cephem-4-carboxylic acid (syn isomer: in the 7-position), mp>140° C. (dec.).
I.R. (Nujol): 3180, 1765, 1715, 1650 cm$^{-1}$.

(32) 7-[2-Methoxyimino-2-(2-aminothiazol-4-yl)-acetamido]-3-[1-(2-carboxy-2-hydroxyethyl)-1H-tetrazol-5-yl]thiomethyl-3-cephem-4-carboxylic acid (syn isomer: in the 7-position), mp 140° to 150° C. (dec.).
I.R. (Nujol): 3320, 1770, 1635 cm$^{-1}$.

(33) 7-[2-Methoxyimino-2-{2-(2,2,2-trifluoroacetamido)-thiazol-4-yl}acetamido]-3-[1-(2-carboxy-2-tert-butoxycarboxamidoethyl)-1H-tetrazol-5-yl]-thiomethyl-3-cephem-4-carboxylic acid (syn isomer: in the 7-position), mp 189° to 196° C. (dec.).
I.R. (Nujol): 1780, 1695 cm$^{-1}$.

(34) 7-[2-Methoxyimino-2-{2-(2,2,2-trifluoroacetamido)-thiazol-4-yl}acetamido]-3-[1-(2-carboxy-2-aminoethyl)-1H-tetrazol-5-yl]thiomethyl-3-cephem-4-carboxylic acid formate (syn isomer: in the 7-position).
I.R. (Nujol): 3160, 1760, 1650 cm$^{-1}$.

(35) 7-[2-Methoxyimino-2-(2-aminothiazol-4-yl)acetamido]-3-[1-(2-carboxy-2-aminoethyl)-1H-tetrazol-5-yl]-thiomethyl-3-cephem-4-carboxylic acid (syn isomer: in the 7-position).
I.R. (Nujol): 1765, 1640 cm$^{-1}$.

(36) 7-Amino-3-[1-(3-carboxy-1-propenyl)-1H-tetrazol-5-yl]thiomethyl-3-cephem-4-carboxylic acid.
I.R. (Nujol): 1795 cm$^{-1}$.
N.M.R. (DMSO-d$_6$, δ): 3.35 (2H, m), 3.63 (2H, ABq, J=18 Hz), 4.33 (2H, ABq, J=14 Hz), 4.75 (1H, d, J=5 Hz), 4.94 (1H, d, J=5 Hz), 6.18 (1H, m), 6.96 (1H, m).

(37) 7-Amino-3-[1-(1-carboxyallyl)-1H-tetrazol-5-yl]-thiomethyl-3-cephem-4-carboxylic acid.
I.R. (Nujol): 1795 cm$^{-1}$.
N.M.R. (DMSO-d$_6$, δ): 3.57 (2H, m), 4.32 (2H, m), 4.84 (2H, m), 5.18–5.40 (2H, m), 5.80–6.47 (2H, m).

(38) 7-[2-Methoxyimino-2-(2-aminothiazol-4-yl)-acetamido]-3-[1-(3-carboxy-1-propenyl)-1H-tetrazol-5-yl]thiomethyl-3-cephem-4-carboxylic acid (syn isomer: in the 7-position).
I.R. (Nujol): 3300, 1760, 1660 cm$^{-1}$.

(39) 7-[2-(2-Propynyloxyimino)-2-(2-aminothiazol-4-yl)-acetamido]-3-[1-(3-carboxy-1-propenyl)-1H-tetrazol-5-yl]thiomethyl-3-cephem-4-carboxylic acid (syn isomer: in the 7-position).
I.R. (Nujol): 3320, 2150, 1775, 1675 cm$^{-1}$.

(40) 7-[2-Methoxyimino-2-(2-aminothiazol-4-yl)-acetamido]-3-[1-(1-carboxyallyl)-1H-tetrazol-5-yl]thiomethyl-3-cephem-4-carboxylic acid (syn isomer: in the 7-position).
I.R. (Nujol): 3350, 1765, 1660, 1605 cm$^{-1}$.

(41) 7-[2-(2-Cyclopenten-1-yl)oxyimino-2-(2-formamidothiazol-4-yl)acetamido]-3-[1-(3-carboxy-1-propenyl)-1H-tetrazol-5-yl]thiomethyl-3-cephem-4-carboxylic acid (syn isomer: in the 7-position).
I.R. (Nujol): 1770, 1660 cm$^{-1}$.

(42) 7-[2-(2-Cyclopenten-1-yl)oxyimino-2-(2-aminothiazol-4-yl)acetamido]-3-[1-(3-carboxy-1-propenyl)-1H-tetrazol-5-yl]thiomethyl-3-cephem-4-carboxylic acid (syn isomer: in the 7-position).
I.R (Nujol): 3280, 1770, 1660 cm$^{-1}$.

(43) 7-[2-Phenoxyimino-2-(2-formamidothiazol-4-yl)acetamido]-3-[1-(3-carboxy-1-propenyl)-1H-tetrazol-5-yl]thiomethyl-3-cephem-4-carboxylic acid (syn isomer: in the 7-position).

N.M.R. (DMSO-d$_6$, δ): 3.33–3.90 (6H, m), 4.10–4.67 (2H, m), 5.23 (1H, d, J=5 Hz); 5.80–6.33 (2H, m), 6.90–7.57 (6H, m), 7.73 (1H, s), 8.60 (1H, s), 9.03 (1H, d, J=8 Hz), 12.86 (1H, broad s).

(44) 7-[2-Phenoxyimino-2-(2-aminothiazol-4-yl)-acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3150, 1770, 1650, 1585 cm$^{-1}$.

EXAMPLE 5

2-(2-Cyclopenten-1-yl)oxyimino-2-(2-formamidothiazol-4-yl)acetic acid (syn isomer) (1.00 g) was added at 0° C. to vilsmeier reagent which had been prepared from N,N-dimethylformamide (0.30 g) and phosphoryl chloride (0.62 g) in ethyl acetate (1.2 ml) and tetrahydrofuran (10 ml), and the mixture was stirred at the same temperature for 30 minutes to afford the activated solution. The activated solution was added dropwise at −5 to 0 C. to a solution of 7-amino-3-[1-(2-carboxy-2-hydroxyiminoethyl)-1H-tetrazol-5-yl]thiomethyl-3-cephem-4-carboxylic acid (1.30 g) in water (8 ml) and acetone (8 ml), adjusted to pH 8.0 with sodium bicarbonate and the mixture was stirred at the same temperature for 30 minutes. To the resultant mixture was added ethyl acetate (10 ml), and the aqueous phase was separated from the mixture. To the aqueous solution was added ethyl acetate (60 ml) and the mixture was adjusted to pH 2.0 with 10% hydrochloric acid with stirring, and the ethyl acetate layer was separated, washed with water, treated with activated carbon, dried over magnesium sulfate and evaporated. The residue was pulverized with diethyl ether to give 7-[2-(2-cyclopenten-1-yl)oxyimino-2-(2-formamidothiazol-4-yl)acetamido]-3-[1-(2-carboxy-2-hydroxyiminoethyl-1H-tetrazol-5-yl]thiomethyl-3-cephem-4-carboxyic acid (syn isomer: in the 7-position) (1.17 g).

I.R. (Nujol): 3200, 1780, 1660 cm$^{-1}$.

N.M.R. (DMSO-d$_6$): 1.75–2.73 (4H, m), 3.73 (2H, m), 4.39 (2H, q, J=14.0 Hz); 5.03–5.53 (4H, m); 5.62–6.36 (3H, m); 7.43 (1H, s), 8.56 (1H, s), 9.63 (1H, d, J=8.0 Hz).

EXAMPLE 6

2-Methoxyimino-2-[2-(2,2,2-trifluoroacetamido)-thiazol-4-yl]acetic acid (syn isomer) (0.97 g) was added at 0° C. to vilsmeier reagent which had been prepared from N,N-dimethylformamide (0.31 g) and phosphoryl chloride (0.65 g) in ethyl acetate (1.2 ml) and tetrahydrofuran (7.4 ml), and the mixture was stirred at the same temperature for 30 minutes to afford the activated solution. The activated solution was added dropwise at −5 to 0 C. to a solution of 7-amino-3-[1-(2-carboxy-2-methoxyiminoethyl)-1H-tetrazol-5-yl]-thiomethyl-3-cephem-4-carboxylic acid (1.40 g) in water (10 ml) and acetone (8 ml), adjusted to pH 8.0 with sodium bicarbonate and the mixture was stirred at the same temperature for 45 minutes. To the resultant mixture was added ethyl acetate (10 ml), and the aqueous phase was separated from the mixture. To the aqueous solution was added ethyl acetate (70 ml) and the mixture was adjusted to pH 2.0 with 10% hydrochloric acid with stirring, and the ethyl acetate layer was separated, washed with a saturated aqueous solution of sodium chloride, dried over magnesium sulfate and evaporated. The residue was pulverized with diisopropyl ether to give 7-[2-methoxyimino-2-{2-(2,2,2-trifluoroacetamido)thiazol-4-yl}acetamido]-3-[1-(2-carboxy-2-methoxyiminoethyl)-1H-tetrazol-5-yl]-thiomethyl-3-cephem-4-carboxylic acid (syn isomer: in the 7-position) (1.77 g), mp 164° to 170° C. (dec.).

I.R. (Nujol): 1780, 1715, 1655 cm$^{-1}$.

N.M.R. (DMSO-d$_6$, δ): 3.70 (2H, m), 3.91 (3H, s); 3.97 (3H, s), 4.39 (2H, m), 5.14 (1H, d, J=4.5 Hz); 5.27 (2H, s), 5.81 (1H, dd, J=4.5 and 8 Hz); 7.52 (1H, s); 9.73 (1H, d, J=8 Hz).

EXAMPLE 7

2-(2-Propynyloxyimino)-2-[2-(2,2,2-trifluoroacetamido)thiazol-4-yl]acetic acid (syn isomer) (1.05 g) was added at 0° C. to vilsmeier reagent which had been prepared from N,N-dimethylformamide (0.31 g) and phosphoryl chloride (0.65 g) in ethyl acetate (1.2 ml) and tetrahydrofuran (7.4 ml), and the mixture was stirred at the same temperature for 30 minutes to afford the activated solution. The activated solution was added dropwise at −5° to 0° C. to a solution of 7-amino 3-[1-(2-carboxy-2-methoxyiminoethyl)-1H-tetrazol-5-yl]thiomethyl-3-cephem-4-carboxylic acid (1.40 g) in water (10 ml) and acetone (8 ml), adjusted to pH 8.0 with sodium bicarbonate and the mixture was stirred at the same temperature for 35 minutes. To the resultant mixture was added ethyl acetate (10 ml), and the aqueous layer was separated from the mixture. To the aqueous solution was added ethyl acetate (70 ml) and the mixture was adjusted to pH 1.8 with 10% hydrochlonic acid with stirring, and the ethyl acetate layer was separated, washed with a saturated aqueous solution of sodium chloride, dried over magnesium sulfate and evaporated. The residue was pulverized with diisopropyl ether to give 7-[2-(2-propynyloxyimino)-2-{2-(2,2,2-trifluoroacetamido)thiazol-4-yl}acetamido]-3-[1-(2-carboxy-2-methoxyiminoethyl)-1H-tetrazol-5-yl]-thiomethyl-3-cephem-4-carboxylic acid (syn isomer: in the 7-position) (2.05 g).

I.R. (Nujol): 3225, 2110, 1770, 1715, 1670 cm$^{-1}$.

N.M.R. (DMSO-d$_6$, δ): 3.47 (1H, m); 3.69 (2H, m); 3.97 (3H, s), 4.35 (2H, m), 4.77 (2H, m), 5.14 (1H, d, J=5 Hz), 5.26 (2H, s); 5.80 (1H, dd, J=5 and 8 Hz); 7.55 (1H, s), 9.80 (1H, d, J=8 Hz).

EXAMPLE 8

The following compounds were prepared according to the similar manners to those of examples 5 to 7.

(1) 7-[2-Methoxyimino-2-(2-formamidothiazol-4-yl)-acetamido]-3-[1-(2-carboxy-2-hydroxyiminoethyl)-1H-tetrazol-5-yl]thiomethyl-3-cephem-4-carboxylic acid (syn isomer: in the 7-position).

I.R. (Nujol): 1760, 1650 cm$^{-1}$.

N.M.R. (DMSO-d$_6$, δ): 3.72 (2H, m), 3.90 (3H, s); 4.36 (2H, m), 5.04–5.46 (3H, m); 5.83 (1H, dd, J=4.0 and 8.0 Hz), 7.43 (1H, s), 8.55 (1H, s); 9.78 (1H, d, J=8.0 Hz).

(2) 7-[2-Cyclopentyloxyimino-2-{2-(2,2,2-trifluoroacetamido)thiazol-4-yl}acetamido]-3-[1-(2-carboxy-2-hydroxyiminoethyl)-1H-tetrazol-5-yl]thiomethyl-3-cephem-4-carboxylic acid (syn isomer: in the 7-position).

I.R. (Nujol): 3150, 1770, 1710, 1660 cm$^{-1}$.

N.M.R. (DMSO-d$_6$, δ): 1.31–2.01 (8H, m), 3.69 (2H, m); 4.35 (2H, m); 4.72 (H, m), 5.14 (1H, d, J=4.0 Hz), 5.27 (2H, s), 5.80 (1H, dd, J=4.0 and 8.0 Hz); 7.48 (1H, s); 9.67 (1H, d, J=8.0 Hz).

(3) 7-[2-(4-Fluorobenzyl)oxyimino-2-{2-(2,2,2-trifluoroacetamido)thiazol-4-yl}acetamido]-3-[1-(2-(2-carboxy-2-hydroxyiminoethyl)-1H-tetrazol-5-yl]thiomethyl-3-cephem-4-carboxylic acid (syn isomer: in the 7-position).
I.R. (Nujol): 3300, 1780, 1720, 1670 cm$^{-1}$.
N.M.R. (DMSO-d$_6$, δ): 3.70 (2H, m), 4.41 (2H, m), 5.04–5.45 (5H, m); 5.87 (1H, dd, J=4.0 and 8.0 Hz); 6.96–7.72 (4H, m); 7.58 (1H, s); 9.88 (1H, d, J=8.0 Hz).

(4) 7-[2-Isopropoxyimino-2-{2-(2,2,2-trifluoroacetamido)-thiazol-4-yl}acetamido]-3-[1-(2-carboxy-2-methoxyiminoethyl)-1H-tetrazol-5-yl]thiomethyl-3-cephem-4-carboxylic acid (syn isomer: in the 7-position).
I.R. (Nujol): 1780, 1715 cm$^{-1}$.
N.M.R. (DMSO-d$_6$, δ): 1.22 (3H, s), 1.33 (3H, s), 3.72 (2H, m), 3.98 (3H, s), 4.21–4.67 (3H, m); 5.17 (1H, d, J=5 Hz), 5.28 (2H,s), 5.83 (1H, dd, J=5 and 8 Hz); 7.48 (1H, s); 9.68 (1H, d, J=8 Hz).

(5) 7-[2-Allyloxyimino-2-(2-formamidothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position).
I.R. (Nujol): 1770, 1670 cm$^{-1}$.
N.M.R. (DMSO-d$_6$, δ): 3.73 (2H, m), 4.02 (3H, s); 4.43 (2H, m); 4.68 (2H, m); 5.10–5.60 (5H, m); 5.77–6.30 (2H, m); 7.46 (1H, s); 8.57 (1H, s), 9.76 (1H, d, J=8 Hz).

(6) 7-[2-(Cyclopenten-1-yl)oxyimino-2-(2-formamidothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position), mp 156° to 161° C. (dec.).
I.R. (Nujol): 1770, 1665 cm$^{-1}$.
N.M.R. (DMSO-d$_6$, δ): 1.70–2.60 (4H, m); 3.67 (2H, m), 3.98 (3H, s); 4.37 (2H, m); 5.02–5.46 (4H, m); 5.71–6.20 (3H, m); 7.39 (1H, s); 8.52 (1H, s); 9.60 (1H, d, J=8 Hz).

(7) 7-[2-Benzyloxyimino-2-{2-(2,2,2-trifluoroacetamido)-thiazol-4-yl}acetamido]-3-[1-(2-carboxy-2-methoxyiminoethyl)-1H-tetrazol-5-yl]thiomethyl-3-cephem-4-carboxylic acid (syn isomer: in the 7-position), mp 165° to 170° C. (dec.).
I.R. (Nujol): 1775, 1710, 1650 cm$^{-1}$.
N.M.R. (DMSO-d$_6$, δ): 3.67 (2H, m), 4.00 (3H, s); 4.37 (2H, m); 5.13–5.50 (5H, m); 5.91 (1H, dd, J=5 and 8 Hz); 7.40 (5H, m), 7.57 (1H, s), 9.88 (1H, d, J=8 Hz).

(8) 7-[2-(4-Fluorobenzyl)oxyimino-2-{2-(2,2,2-trifluoroacetamido)thiazol-4-yl}acetamido]-3-[1-(2-carboxy-2-methoxyiminoethyl)-1H-tetrazol-5-yl]thiomethyl-3-cephem-4-carboxylic acid (syn isomer: in the 7-position, (mp 153° C. (dec.).
I.R. (Nujol): 1765, 1710, 1650 cm$^{-1}$.
N.M.R. (DMSO-d$_6$, δ): 3.65 (2H, m), 3.97 (3H, s), 4.37 (2H, m), 5.08–5.40 (5H, m); 5.83 (1H, dd, J=5 and 8 Hz); 7.03–7.63 (5H, m), 9.88 (1H, d, J=8 Hz).

(9) 7-[2-(2-Cyclopenten-1-yl)oxyimino-2-(2-formamidothiazol-4-yl)acetamido]-3-[1-(2-carboxy-2-allyloxyiminoethyl)-1H-tetrazol-5-yl]-thiomethyl-3-cephem-4-carboxylic acid (syn isomer: in the 7-position), mp 150° to 160° C. (dec.).
I.R. (Nujol): 1775, 1670 cm$^{-1}$.
N.M.R. (DMSO-d$_6$, δ): 1.77–2.70 (4H, m); 3.70 (2H, m); 4.40 (2H, ABq, J=14 Hz); 4.77 (2H, m); 5.03–5.50 (6H, m); 5.63–6.30 (4H, m); 7.40 (1H, s); 8.57 (1H, s), 9.62 (1H, d, J=8 Hz).

(10) 7-[2-Benzyloxyimino-2-{2-(2,2,2-trifluoroacetamido)thiazol-4-yl}acetamido]-3-[1-(2-carboxy-2-allyloxyiminoethyl)-1H-tetrazol-5-yl]thiomethyl-3-cephem-4-carboxylic acid (syn isomer: in the 7-position).
I.R. (Nujol): 1775, 1710, 1650 cm$^{-1}$.
N.M.R. (DMSO-d$_6$, δ): 3.70 (2H, m), 4.30 (2H, m); 4.80 (2H, m); 5.07–5.60 (7H, m); 5.68–6.21 (2H, m); 7.42 (5H, m); 7.56 (1H, s), 9.88 (1H, d, J=8 Hz).

(11) 7-[2-(4-Fluorobenzyl)oxyimino-2-{2-(2,2,2-trifluoroacetamido)thiazol-4-yl}acetamido]-3-[1-(2-carboxy-2-hydroxyethyl)-1H-tetrazol-5-yl]thiomethyl-3-cephem-4-carboxylic acid (syn isomer: in the 7-position), mp 90° to 100° C. (dec.).
I.R. (Nujol): 1770, 1710, 1650 cm$^{-1}$.
N.M.R. (DMSO-d$_6$, δ): 3.73 (2H, m); 4.20–4.80 (5H, m), 5.10–5.47 (3H, m); 5.88 (1H, dd, J=5 and 8 Hz); 6.88–7.70 (5H, m); 9.89 (1H, d, J=8 Hz).

(12) 7-[2-Methoxyimino-2-(2-aminothiazol-4-yl)-acetamido]-3-[1-(2-carboxy-2-hydroxyiminoethyl)-1H-tetrazol-5-yl]thiomethyl-3-cephem-4-carboxylic acid (syn isomer: in the 7-position), mp 169° to 173° C. (dec.).
I.R. (Nujol): 3300, 3200, 1770, 1660, 1630 cm$^{-1}$.

(13) 7-[2-Cyclopentyloxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 168° to 171° C. (dec.).
I.R. (Nujol): 3250, 3150, 1760, 1650 cm$^{-1}$.

(14) 7-[2-(2-cyclopenten-1-yl)oxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 150° to 160° C. (dec.).
I.R. (Nujol): 3270, 3160, 1770, 1650 cm$^{-1}$.

(15) 7-[2-(4-Fluorobenzyl)oxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 160° to 163° C.
I.R. (Nujol): 3200, 1770, 1640 cm$^{-1}$.

(16) 7-[2-Methoxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position).
I.R. (Nujol): 3270, 1770, 1645 cm$^{-1}$.

(17) 7-[2-Isopropoxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position), mp 140° to 150° C. (dec.).
I.R. (Nujol): 3260, 1770, 1660 cm$^{-1}$.

(18) 7-[2-Allyloxyimino-2-(2-aminothiazol-4-yl)-acetamido[-3-[1-(2-carboxy-2-methoxyiminoethyl)-1H-tetrazol-5-yl]thiomethyl-3-cephem-4-carboxylic acid (syn isomer: in the 7-position), mp 130° to 140° C. (dec.).
I.R. (Nujol): 3250, 1770, 1650 cm$^{-1}$.

(19) 7-[2-(2-Propynyloxyimino)-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position).
I.R. (Nujol): 3255, 1775, 1670, 1630 cm$^{-1}$.

(20) 7-[2-(2-Cyclopenten-1-yl)oxyimino-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position), mp 140° to 150° C. (dec.).
I.R. (Nujol): 3260, 1770, 1650 cm$^{-1}$.

(21) 7-[2-Benzyloxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position), mp 168° to 172° C. (dec.).

I.R. (Nujol): 3260, 1770, 1655 cm$^{-1}$.

(22) 7-[2-(4-Fluorobenzyl)oxyimino-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position), mp 130° to 140° C. (dec.).

I.R. (Nujol): 3270, 1770, 1625 cm$^{-1}$.

(23) 7-[2-(2-Cyclopenten-1-yl)oxyimino-2-(2-aminothiazol-4-yl)acetamido]-3-[1-(2-carboxy-2-allyloxyiminoethyl)-1H-tetrazol-5-yl]thiomethyl-3-cephem-4-carboxylic acid (syn isomer: in the 7-position), mp 140° to 150° C. (dec.).

I.R.(Nujol): 3270, 1770, 1660, 1630 cm$^{-1}$.

(24) 7-[2-Benzyloxyimino-2-(2-aminothiazol-4-yl)-acetamido-3-[1-(2-carboxy-2-allyloxyiminoethyl)-1H-tetrazol-5-yl]thiomethyl-3-cephem-4-carboxylic acid (syn isomer: in the 7-position), mp 180° to 190° C. (dec.).

I.R. (Nujol): 3290, 1775, 1705, 1655 cm$^{-1}$.

(25) 7-[2-(4-Fluorobenzyl)oxyimino-2-(2-aminothiazol-4-yl)acetamido]-3-[1-(2-carboxy-2-hydroxyechyl)-1H-tetrazol-5-yl]thiomethyl-3-cephem-4-carboxylic acid (syn isomer: in the 7-position).

I.R. (Nujol): 3280, 1765, 1630 cm$^{-1}$.

(26) 7-[2-Methoxyimino-2-{2-(2,2,2-trifluoroacetamido)-thiazol-4-yl}acetamido]-3-[1-(2-carboxy-2-hydroxyethyl)-1H-tetrazol-5-yl]thiomethyl-3-cephem-4-carboxylic acid (syn isomer: in the 7-position), mp>140° C. (dec.).

I.R. (Nujol): 3180, 1765, 1715, 1650 cm$^{-1}$.

N.M.R. (DMSO-d$_6$, δ): 3.70 (2H, m), 3.91 (3H, s), 4.20–4.77 (5H, m), 5.13 (1H, d, J=5 Hz), 5.75 (1H, dd, J=5 and 8 Hz), 7.52 (1H, s), 9.75 (1H, d, J=8 Hz).

(27) 7-[2-Methoxyimino-2-(2-aminothiazol-4-yl)-acetamido]-3-[1-(2-carboxy-2-hydroxyethyl)-1H-tetrazol-5-yl]thiomethyl-3-cephem-4-carboxylic acid (syn isomer: in the 7-position), mp 140° to 150° C. (dec.).

I.R. (Nujol): 3320, 1770, 1635 cm$^{-1}$.

(28) 7-[2-Methoxyimino-2-{2-(2,2,2-trifluoroacetamido)thiazol-4-yl}acetamido]-3-[1-(2-carboxy-2-tertbutoxycarboxamidoethyl)-1H-tetrazol-5-yl]-thiomethyl-3-cephem-4-carboxylic acid (syn isomer: in the 7-position), mp 189° to 196° C. (dec.).

I.R. (Nujol): 1780, 1695 cm$^{-1}$.

N.M.R. (DMSO-d$_6$, δ): 1.30 (9H, s), 3.70 (2H, m), 3.89 (3H, s), 4.22–4.70 (5H, m), 5.12 (1H, d, J=5 Hz), 5.80 (1H, dd, J=5 and 8 Hz), 7.52 (1H, s), 9.73 (1H, d, J=8 Hz).

(29) 7-[2-Methoxyimino-2-{2-(2,2,2-trifluoroacetamido)thiazol-4-yl}acetamido]-3-[1-(2-carboxy-2-aminoethyl)-1H-tetrazol-5-yl]thiomethyl-3-cephem-4-carboxylic acid formate (syn isomer: in the 7-position).

I.R. (Nujol): 3160, 1760, 1650 cm$^{-1}$.

(30) 7-[2-Methoxyimino-2-(2-aminothiazol-4-yl)acetamido]-3-[1-(2-carboxy-2-aminoethyl)-1H-tetrazol-5-yl]-thiomethyl-3-cephem-4-carboxylic acid (syn isomer: in the 7-position).

I.R. (Nujol): 1765, 1640 cm$^{-1}$.

(31) 7-[2-Methoxyimino-2-(2-aminothiazol-4-yl)-acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3300, 1760, 1660 cm$^{-1}$.

N.M.R. (DMSO-d$_6$, δ): 3.63 (2H, m), 3.87 (3H, s), 4.40 (2H, ABq, J=14 Hz); 5.03 (3H, m), 5.67 (2H, m), 6.30 (1H, m), 6.73 (1H, s); 7.27 (2H, broad s), 9.57 (1H, d, J=8 Hz).

(32) 7-[2-(2-Propynyloxyimino)-2-{2-(2,2,2-trifluoroacetamido)thiazol-4-yl}acetamido]-3-[1-(3-carboxy-1-propenyl)-1H-tetrazol-5-yl]-thiomethyl-3-cephem-4-carboxylic acid (syn isomer: in the 7-position).

I.R. (Nujol): 2120, 1780, 1720 cm$^{-1}$.

N.M.R. (DMSO-d$_6$, δ): 3.47–3.70 (5H, m); 4.33–4.47 (2H, m); 4.80 (2H, m), 5.20 (1H, d, J=5 Hz), 5.77–6.34 (2H, m), 6.77–7.10 (1H, m), 7.63 (B 1H, s), 10.27 (1H, d, J=8 Hz).

(33) 7-[2-(2-Propynyloxyimino)-2-(2-aminothiazol-4-yl)acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3320, 2150, 1775, 1675 cm$^{-1}$.

(34) 7-[2-Methoxyimino-2-(2-aminothiazol-4-yl)-acetamido]-3-[1-(1-carboxyallyl)-1H-tetrazol-5-yl]thiomethyl-3-cephem-4-carboxylic acid (syn isomer: in the 7-position).

I.R. (Nujol): 3350, 1765, 1660, 1605 cm$^{-1}$.

N.M.R. (DMSO-d$_6$, δ): 3.55 (2H, m); 3.87 (3H, s); 4.37 (2H, m); 4.67–4.83 (5H, m); 6.75 (1H, s), 7.30 (2H, broad s); 9.60 (1H, d, J=8 Hz).

(35) 7-[2-(2-Cyclopenten-1-yl)oxyimino-2-(2-formamidothiazol-4-yl)acetamido]-3-[1-(3-carboxy-1-propenyl)-1H-tetrazol-5-yl]thiomethyl-3-cephem-4-carboxylic acid (syn isomer: in the 7-position).

I.R. (Nujol): 1770, 1660 cm$^{-1}$.

(36) 7-[2-(2-Cyclopenten-1-yl)oxyimino-2-(2-aminothiazol-4-yl)acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3280, 1770, 1660 cm$^{-1}$.

(37) 7-[2-Phenoxyimino-2-(2-formamidothiazol-4-yl)-acetamido]-3-[1-(3-carboxy-1-propenyl)-1H-tetrazol-5-yl]thiomethyl-3-cephem-4-carboxylic acid (syn isomer: in the 7-position).

N.M.R. (DMSO-d$_6$, δ): 3.33–3.90 (6H, m); 4.10–4.67 (2H, m); 5.23 (1H, d, J=5 Hz); 5.80–6.33 (2H, m); 6.90–7.57 (6H, m); 7.73 (1H, s); 8.60 (1H, s); 9.03 (1H, d, J=8 Hz); 12.86 (1H, broad s).

(38) 7-[2-Phenoxyimino-2-(2-aminothiazol-4-yl)-acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3150, 1770, 1650, 1585 cm$^{-1}$.

EXAMPLE 9

A solution of 7-[2-(2-cyclopenten-1-yl)oxyimino-2-(2-formamidothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position) (1.1 g) and conc. hydrochloric acid (0.12 g) in methanol (10 ml) and tetrahydrofuran (2 ml) was stirred at room temperature for 2.5 hours. After removal of organic solvents under reduced pressure, the residue was dissolved in an aqueous solution of sodium bicarbonate and the solution was adjusted to pH 7.5. The aqueous solution was washed with ethyl acetate (15 ml) and then adjusted to pH 3.0 with 10% hydrochloric acid to give precipitates which were filtered and washed with water to give 7-[2-(2-cyclopenten-1-yl)oxyimino-2-(2-aminothiazol-4-yl)acetamido]-3-[1-(2-carboxy-2-hydroxyiminoethyl)-1H-tetrazole-5-yl]thiomethyl-3-cephem-4-carboxylic acid (syn isomer: in the 7-position).

I.R. (Nujol): 3270, 3160, 1770, 1650 cm$^{-1}$.

N.M.R. (DMSO-d$_6$, δ): 1.78–2.80 (4H, m), 3.70 (2H, m), 4.38 (2H, q, J=14.0 Hz), 4.97–5.51 (4H, m), 5.61–6.31 (3H, m), 6.73 (1H, ), 9.53 (1H, d, J=8.0 Hz).

EXAMPLE 10

A mixture of 7-[2-methoxyimino-2-{2-(2,2,2-trifluoroacetamido)thiazol-4-yl}acetamido]-3-[1-(2-carboxy-2-methoxyiminoethyl)-1H-tetrazol-5-yl]-thiomethyl-3-cephem-4-carboxylic acid (syn isomer: in the 7-position) (1.70 g) and sodium acetate trihydrate (3.26 g) in water (14 ml) was stirred overnight at room temperature. The solution was adjusted to pH 2.5 with 10% hydrochloric acid under ice-cooling and the resultant precipitates were filtered and washed with water to give 7-[2-methoxyimino-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position).

I.R. (Nujol): 3270, 1770, 1645 cm$^{-1}$.

N.M.R. (DMSO-d$_6$, δ): 9.60 (1H, d, J=8 Hz); 7.13 (2H, broad s); 6.72 (1H, s); 5.77 (1H, dd, J=5 and 8 Hz); 5.25 (2H, s), 5.09 (1H, d, J=8 Hz); 4.32 (2H, ABq, J=14 Hz); 3.95 (3H, s); 3.80 (3H, s); 3.65 (2H, broad s).

EXAMPLE 11

A mixture of 7-[2-(2-propynyloxyimino)-2-{2-(2,2,2-trifluoroacetamido)thiazol-4-yl}acetamido]-3-[1-(2-carboxy-2-methoxyiminoethyl)-1H-tetrazol-5-yl]-thiomethyl-3-cephem-4-carboxylic acid (syn isomer: in the 7-position) (2.0 g) and sodium acetate.trihydrate (3.71 g) in water (15 ml) was stirred overnight at room temperature. The solution was adjusted to pH 2.5 with 10% hydrochloric acid under ice-cooling and the resultant precipitates were filtered and washed with water to give 7-[2-(2-propynyloxyimino)-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position).(1.12 g).

I.R. (Nujol): 3255, 1775, 1670, 1630 cm$^{-1}$.

N.M.R. (DMSO-d$_6$, δ): 9.57 (1H, d, J=8 Hz); 7.17 (2H, broad s); 6.70 (1H, s); 5.73 (1H, dd, J=5 and 8 Hz); 5.22 (2H, s); 5.07 (1H, d, J=5 Hz); 4.64 (2H, m); 4.33 (2H, m); 3.95 (3H, s); 3.63 (2H, m); 3.40 (1H, m).

EXAMPLE 12

The following compounds were prepared according to the similar manners to those of Examples 9 to 11.

(1) 7-[2-Methoxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 169° to 173° C. (dec.).

I.R. (Nujol): 3300, 3200, 1770, 1660, 1630 cm$^{-1}$.

N.M.R. (DMSO-d$_6$, δ): 3.70 (2H, m); 3.86 (3H, s); 4.36 (2H, q, J=14.0 Hz), 4.98–5.39 (3H, m); 5.80 (1H, dd, J=4.0 and 8.0 Hz); 6.77 (1H, s), 9.60 (1H, d, J=8.0 Hz).

(2) 7-[2-Cyclopentyloxyimino-2-(2-aminothiazol-4-yl)acetamido]-3-[1-(2-carboxy-2-hydroxyiminoethyl)-1H-tetrazol-5-yl]thiomethyl-3-cephem-4-carboxyclic acid (syn isomer: in the 7-position), mp 168° to 171° C. (dec.).

I.R. (Nujol): 3250, 3150, 1760, 1650 cm$^{-1}$.

N.M.R. (DMSO-d$_6$, δ): 1.28–2.03 (8H, m), 3.67 (2H, m), 4.33 (2H, m), 4.86 (1H, m), 4.99–5.46 (3H, m), 5.73 (1H, dd, J=5 and 8.0 Hz), 6.67 (1H, s), 9.49 (1H, d, J=8.0 Hz).

(3) 7-[2-(4-Fluorobenzyl)oxyimino-2-(2-aminothiazol-4-yl)acetamido]-3-[1-(2-carboxy-2-hydroxyiminoethyl)-1H-tetrazol-5-yl]thiomethyl-3-cephem-4-carboxylic acid (syn isomer: in the 7-position), mp 160° to 163° C.

I.R. (Nujol): 3200, 1770, 1640 cm$^{-1}$.

N.M.R. (DMSO-d$_6$, δ): 3.69 (2H, m), 4.41 (2H, q, J=14.0 Hz), 5.03–5.48 (5H, m), 5.84 (1H, dd, J=5.0 and 8.0 Hz), 6.81 (1H, s), 6.89–7.70 (4H, m), 9.72 (1H, d, J=8.0 Hz).

(4) 7-[2-Isopropoxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position), mp 140° to 150° C.

I.R. (Nujol): 3260, 1770, 1660 cm$^{-1}$.

N.M.R. (DMSO-d$_6$): 1.27 (6H, d, J=6 Hz); 3.68 (2H, m); 3.98 (3H, s); 4.22–4.50 (3H, m); 5.16 (1H, d, J=5 Hz); 5.27 (2H, s); 5.77 (1H, dd, J=5 and 8 Hz); 6.73 (1H, s); 9.55 (1H, d, J=8 Hz).

(5) 7-[2-Allyloxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position), mp 130° to 140° C. (dec.).

I.R. (Nujol): 3250, 1770, 1650 cm$^{-1}$.

N.M.R. (DMSO-d$_6$, δ): 3.73 (2H, m), 4.02 (3H, s); 4.40 (2H, m), 4.65 (2H, m), 5.31 (2H, s); 5.60–5.07 (3H, m); 6.40–5.70 (2H, m); 7.82 (1H, s); 9.69 (1H, d, J=8 Hz).

(6) 7-[2-(2-Cyclopenten-1-yl)oxyimino-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position), mp 140° to 150° C. (dec.).

I.R. (Nujol): 3260, 1770, 1650 cm$^{-1}$.

N.M.R. (DMSO-d$_6$, δ): 1.80–2.43 (4H, m); 3.63 (2H, m); 3.97 (3H, s); 4.35 (2H, m); 5.03–5.43 (4H, m); 5.60–6.20 (3H, m); 6.69 (1H, s); 9.50 (1H, d, J=8 Hz).

(7) 7-[2-Benzyloxyimino-2-(2-aminothiazol-4-yl)-acetamido]-3-[1-(2-carboxy-2-methoxyiminoethyl)-1H-tetrazol-5-yl]thiomethyl-3-cephem-4-carboxylic acid (syn isomer: in the 7-position), mp 168° to 172° C. (dec.).

I.R. (Nujol): 3260, 1770, 1655 cm$^{-1}$.

N.M.R. (DMSO-d$_6$, δ): 3.67 (2H, m), 4.00 (3H, s), 4.37 (2H, ABq, J=14 Hz); 5.17 (3H, m); 5.30 (2H, s); 5.84 (1H, dd, J=5 and 8 Hz); 6.75 (1H, s); 7.37 (5H, m); 9.67 (1H, d, J=8 Hz).

(8) 7-[2-(4-Fluorobenzyl)oxyimino-2-(2-aminothiazol-4-yl)acetamido]-3-[1-(2-carboxy-2-methoxyiminoethyl)-1H-tetrazol-5-yl]thiomethyl-3-cephem-4-carboxylic acid (syn isomer: in the 7-position), mp 130° to 140° C. (dec.).

I.R. (Nujol): 3270, 1770, 1625 cm$^{-1}$.

N.M.R. (DMSO-d$_6$, δ): 3.63 (2H, m); 3.95 (3H, s); 4.33 (2H, ABq, J=14 Hz); 5.11 (3H, m); 5.24 (2H, s); 5.79 (1H, dd, J=5 and 8 Hz); 6.73 (1H, s), 6.97–7.60 (4H, m); 9.66 (1H, d, J=8 Hz).

(9) 7-[2-(2-Cyclopenten-1-yl)oxyimino-2-(2-aminothiazol-4-yl)acetamido]-3-[1-(2-carboxy-2-allyloxyiminoethyl)-1H-tetrazol-5-yl]thiomethyl-3-cephem-4-carboxylic acid (syn isomer: in the 7-position), mp 140° to 150° C. (dec.).

I.R. (Nujol): 3270, 1770, 1660, 1630 cm$^{-1}$.

N.M.R. (DMSO-d$_6$, δ): 1.70–2.43 (4H, m), 3.67 (2H, m), 4.35 (2H, m), 4.73 (2H, m), 5.00–6.30 (10H, m), 6.70 (1H, s), 9.48 (1H, d, J=8 Hz).

(10) 7-[2-Benzyloxyimino-2-(2-aminothiazol-4-yl)-acetamido]-3-[1-(2-carboxy-2-allyloxyiminoethyl)-1H-tetrazol-5-yl]thiomethyl-3-cephem-4-carboxylic acid (syn isomer: in the 7-position), mp 180° to 190° C. (dec.).

I.R. (Nujol): 3290, 1775, 1705, 1655 cm$^{-1}$.

N.M.R. (DMSO-d$_6$, δ): 3.68 (2H, m); 4.40 (2H, m); 4.77 (2H, m); 5.03–5.50 (7H, m); 5.66–6.29 (2H, m); 6.77 (1H, s); 7.39 (5H, m); 9.71 (1H, d, J=8 Hz).

(11) 7-[2-(4-Fluorobenzyl)oxyimino-2-(2-aminothiazol-4-yl)acetamido]-3-[1-(2-carboxy-2-hydroxyethyl)-1H-tetrazol-5-yl]thiomethyl-3-cephem-4-carboxylic acid (syn isomer: in the 7-position).

I.R. (Nujol): 3280, 1765, 1630 cm$^{-1}$.

N.M.R. (DMSO-d$_6$, δ): 3.70 (2H, m); 4.20–4.70 (5H, m); 5.17 (3H, m); 5.82 (1H, dd, J=5 and 8 Hz); 6.80 (1H, s); 7.03–7.61 (4H, m); 9.73 (1H, d, J=8 Hz).

(12) 7-[2-Methoxyimino-2-(2-aminothiazol-4-yl)-acetamido]-3-[1-(2-carboxy-2-hydroxyethyl)-1H-tetrazol-5-yl]thiomethyl-3-cephem-4-carboxylic acid (syn isomer: in the 7-position), mp 140° to 150° C. (dec.).

I.R. (Nujol): 3320, 1770, 1635 cm$^{-1}$.

N.M.R. (DMSO-d$_6$, δ): 3.70 (2H, m); 3.86 (3H, s); 4.13–4.78 (5H, m); 5.11 (1H, d, J=5 Hz); 5.76 (1H, dd, J=5 and 8 Hz); 6.77 (1H, s); 9.62 (1H, d, J=8 Hz).

(13) 7-[2-Methoxyimino-2-(2-aminothiazol-4-yl)-acetamido]-3-[1-(2-carboxy-2-aminoethyl)-1H-tetrazol-5-yl]thiomethyl-3-cephem-4-carboxylic acid (syn isomer: in the 7-position).

I.R. (Nujol): 1765, 1640 cm$^{-1}$.

N.M.R. (DMSO-d$_6$, δ): 3.72 (2H, m), 3.84 (3H, s), 4.00–4.91 (5H, m), 5.10 (1H, d, J=5 Hz), 5.75 (1H, dd, J=5 and 8 Hz), 6.74 (1H, s), 9.56 (1H, d, J=8 Hz).

(14) 7-[2-Methoxyimino-2-(2-aminothiazol-4-yl)-acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3300, 1760, 1660 cm$^{-1}$.

(15) 7-[2-(2-Propynyloxyimino)-2-(2-aminothiazol-4-yl)-acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3320, 2150, 1775, 1675 cm$^{-1}$.

N.M.R. (DMSO-d$_6$, δ): 3.37 (2H, d, J=6 Hz), 3.47 (1H, m), 3.70 (2H, m), 4.37 (2H, d, J=5 Hz), 4.70 (2H, d, J=2 Hz), 5.10 (1H, d, J=6 Hz), 5.77 (1H, d,d, J=8 and 6 Hz), 6.30 (1H, ddd, J=2, 10 and 12 Hz), 6.77 (1H, s), 7.00 (1H, m), 7.27 (2H, broad), 9.67 (1H, d, J=8 Hz).

(16) 7-[2-Methoxyimino-2-(2-aminothiazol-4-yl)-acetamido]-3-[1-(1-carboxyallyl)-1H-tetrazol-5-yl]thiomethyl-3-cephem-4-carboxylic acid (syn isomer: in the 7-position).

I.R. (Nujol): 3350, 1765, 1660, 1605 cm$^{-1}$.

(17) 7-[2-(2-Cyclopenten-1-yl)oxyimino-2-(2-aminothiazol-4-yl)acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3280, 1770, 1660 cm$^{-1}$.

N.M.R. (DMSO-d$_6$, δ): 1.81–2.93 (4H, m), 3.40 (2H, q, J=16.0 Hz); 3.71 (2H, m), 4.39 (2H, q, J=14.0 Hz); 5.06–5.54 (2H, m); 5.62–6.43 (4H, m); 6.74 (1H, s); 7.01 (1H, d), 9.53 (1H, d; J=8.0 Hz).

(18) 7-[2-Phenoxyimino-2-(2-aminothiazol-4-yl)-acetamido]-3-[1-(3-carboxy-1-propenyl)-1H-tetrazol-5-yl]thiomethyl-3-cephem-4-carboxylic acid (syn isomer: in the 7-position).

I.R. (Nujol): 3150, 1770, 1650, 1585 cm$^{-1}$.

N.M.R. (DMSO-d$_6$, δ): 3.37 (2H, m); 3.73 (2H, broad s); 4.37 (2H, q, J=12 Hz); 5.17 (1H, d, J=5 Hz); 5.73–6.37 (2H, m); 6.87–7.33 (6H, m); 7.00 (1H, s); 9.80 (1H, d, J=8 Hz).

EXAMPLE 13

A solution of 7-[2-methoxyimino-2-{2-(2,2,2-trifluoroacetamido)thiazol-4-yl}acetamido]-3-[1-(2-carboxy-2-tert-butoxycarboxamidoethyl)-1H-tetrazol-5-yl]thiomethyl-3-cephem-4-carboxylic acid (syn isomer: in the 7-position) (1.1 g) in formic acid (11 ml) was stirred for 3 hours at 35° to 40° C. The reaction mixture was concentrated. The residue was pulverized in acetonitril (25 ml) and stirred vigorously. The precipitates were collected by filtration and successively washed with acetonitril and diethyl ether to give 7-[2-methoxyimino-2-{2-(2,2,2-trifluoroacetamido)thiazol-4-yl}acetamido]-3-[1-(2-carboxy-2-aminoethyl)-1H-tetrazol-5-yl]thiomethyl-3-cephem-4-carboxylic acid.formate (syn isomer: in the 7-position).

I.R. (Nujol): 3160, 1760, 1650 cm$^{-1}$.

N.M.R. (DMSO-d$_6$, δ): 3.73 (2H, m); 3.88 (3H, s); 4.00–4.83 (5H, m); 5.13 (1H, d, J=5 Hz), 5.87 (1H, dd, J=5 and 8 Hz), 7.33 (1H, s), 9.68 (1H, d, J=8 Hz).

EXAMPLE 14

The following compound was prepared according to the similar manner to that of Example 13. 7-[2-Methoxyimino-2-(2-aminothiazol-4-yl)acetamido]-3-[1-(2-carboxy-2-aminoethyl)-1H-tetrazol-5-yl]thiomethyl-3-cephem-4-carboxylic acid (syn isomer: in the 7-position).

I.R. (Nujol): 1765, 1640 cm$^{-1}$.

What we claim is:

1. A 1-substituted-1H-tetrazole-5-thiol compound of the formula:

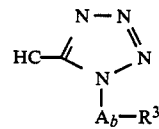

wherein

A$_b$ is hydroxy(lower)alkylene, amino(lower)alkylene, protected amino(lower)alkylene, lower alkenylene, lower alkylene having an oxo group, or hydroxyimino(lower)alkylene wherein the hydrogen atom of the hydroxyimino group may be replaced with a lower aliphatic hydrocarbon group, and R$^3$ is carboxy or a protected carboxy group, and a salt thereof.

2. The compound of claim 1, wherein

A$_b$ is hydroxy(lower)alkylene, amino(lower)alkylene, lower alkoxycarbonylamino(lower)alkylene, hydroxyimino(lower)alkylene, alkoxyimino(lower)alkylene, alkenyloxyimino(lower)alkylene, lower alkenylene or lower alkylene having an oxo group;

R$^3$ is carboxy.

* * * * *